US006211146B1

(12) United States Patent
Kuberasampath et al.

(10) Patent No.: US 6,211,146 B1
(45) Date of Patent: *Apr. 3, 2001

(54) 60A PROTEIN-INDUCED MORPHOGENESIS

(75) Inventors: Thangavel Kuberasampath, Medway, MA (US); Roy H. L. Pang, Etna, NH (US); Hermann Oppermann, Medway, MA (US); David C. Rueger, Hopkinton, MA (US); Charles M. Cohen, Medway, MA (US)

(73) Assignee: Curis, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 08/271,556

(22) Filed: Jul. 7, 1994

Related U.S. Application Data

(63) Continuation of application No. 07/945,292, filed on Sep. 15, 1992, now abandoned, which is a continuation-in-part of application No. 07/922,813, filed on Jul. 31, 1992, now abandoned, which is a continuation-in-part of application No. 07/752,764, filed on Aug. 30, 1991, now abandoned, which is a continuation-in-part of application No. 07/667,274, filed on Mar. 11, 1991, now abandoned, and a continuation-in-part of application No. 07/923,780, filed on Jul. 31, 1992, now abandoned, which is a continuation-in-part of application No. 07/752,764, filed on Aug. 30, 1991, now abandoned, and a continuation-in-part of application No. 07/752,857, filed on Aug. 30, 1991, now abandoned, which is a continuation-in-part of application No. 07/667,274, filed on Mar. 11, 1991, now abandoned, and a continuation-in-part of application No. 07/753,059, filed on Aug. 30, 1991, now abandoned, which is a continuation-in-part of application No. 07/667,274, filed on Mar. 11, 1991, now abandoned.

(51) Int. Cl.[7] .......................... A61K 38/16; A61K 38/18
(52) U.S. Cl. .................. 514/12; 514/2; 424/484; 424/422; 424/426; 424/520
(58) Field of Search .................. 424/484, 422, 424/426, 520; 514/2, 12; 530/399

(56) References Cited

U.S. PATENT DOCUMENTS

| | | | |
|---|---|---|---|
| 4,904,259 | * | 2/1990 | Itay .......................... 530/838 |
| 4,968,590 | | 11/1990 | Kuberasampath et al. .......... 530/326 |
| 4,975,526 | | 12/1990 | Kuberasampath et al. .......... 530/350 |
| 4,983,581 | * | 1/1991 | Antoniades et al. .................... 514/12 |
| 5,011,691 | | 4/1991 | Oppermann et al. ................. 424/423 |
| 5,091,513 | | 2/1992 | Huston et al. ..................... 530/387.3 |
| 5,108,989 | * | 4/1992 | Amento et al. ........................ 514/12 |
| 5,393,739 | * | 2/1995 | Bentz et al. ............................. 514/12 |
| 5,409,896 | * | 4/1995 | Ammann et al. ....................... 514/13 |

FOREIGN PATENT DOCUMENTS

| | | |
|---|---|---|
| 1128881 | 8/1982 | (CA) . |
| 8909788 | * 10/1989 | (WO) . |
| 90/10018 | 9/1990 | (WO) . |
| 91/18558 | 12/1991 | (WO) . |

OTHER PUBLICATIONS

Wozney et al., *Science*, 242:1528–1534 (1988).
Wang et al., *PNAS*, 85:9484–9488 (1988).
Rosen et al.; Wang et al. and Wozney et al., *Calcified Tissue Int 42* (Suppl.): A35 (136), A37 (146, 147) 3 Abstracts (1988).
Rosen et al., *Connect Tissue Res*, 20 (1–4):313–9 (1989).
Wozney et al., *Progress In Growth Factor Research*, 1:267–280 (1990).
2 Abstracts Rosen et al., Celeste et al., *J Cell Biochem Suppl.*, 0 (14 Part E): 33(004, 54(105) (1990).
Katagiri et al., *Biochem Biopys Res*, (172(1):295–299 (1990).
Wozney et al., *Journal Of Cell Science Suppl.*, 13:149–156 (1990).
Takuwa et al., *Biochem Biophys Res Comm*, 174(1):96–101 (1991).
Yamaguchi et al., *J Cell Biol*, 113 (3):681–7 (1991).
Abstract Q–105 D'Alessandro et al., *Journal of Cellular Biochemistry*, (1991) p166.
Abstract Q–111, *Journal Of Cellular Biochemistry*, (1991). p168.
Thies et al., *Endocrinology*, 130 (3):1318–1324 (1992).
Wozney et al., *Mol Reprod Dev*, 32 (2):160–167 (1992).
Rogers et al., *Mol Biol Cell*, 3 (2):189–196 (1992).
3 Abstracts Wozney et al.; Celeste et al.; and Rosen et al., *J Cell Biochem Suppl*, 0 (16 Part F): 76(W026); 100(W502); 103(W513) (1996).
Israel et al. *Growth Factors*, 7:139–150 (1992).
Padgett et al., *Proc. Natl. Acad. Sci. USA*, 90:2905–2909 (1993).
Edelman, G.M., *Ann. Rev. Cell Biol.*, 2:81–116 (1986).
Lee, *PNAS*, 88:4250–4254 (1991).
Panganiban et al., *Mol. and Cell Biol.*, 10:2669–2677 (1990).
Sampath et al., *PNAS*, 80:6591–6595 (1983).
Wharton et al., *PNAS*, 88:9214–9218 (1991).
Wong et al., *PNAS*, 72:3167–3171 (1975).
Wharton et al "Drosophila 60A Gene . . . " *PNAS* 88:9214–9218 (Oct. 1991).*
Daopin et al "Crystal Structure of Transforming Growth Factor—p2 . . ." *Science* 257:369–373 (Jul. 1992).*
Doctor et al "Sequence, Biochemical Characterization . . . " *Dev. Biol.* 151(2): 491–505 (Jun. 1992).*

* cited by examiner

Primary Examiner—Elizabeth Kemmerer
(74) Attorney, Agent, or Firm—Mintz, Levin, Cohn, Ferris, Glovsky & Popeo, P.C.; Ivor R. Elrifi; Michel Morency

(57) ABSTRACT

Disclosed are methods of utilizing a morphogenically active fragment of 60A protein to induce tissue morphogenesis, including methods for increasing a progenitor cell population in a mammal, methods for stimulating progenitor cells to differentiate and maintain their differentiated phenotype in vivo or in vitro, methods for inducing tissue-specific growth in vivo and methods for the replacement of diseased or damaged tissue in vivo.

8 Claims, No Drawings

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 1368 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..1365

(xi) SEQUENCE DESCRIPTION: SEQ ID NO:1:

```
ATG TCG GGA CTG CGA AAC ACC TCG GAG GCC GTT GCA GTG CTC GCC TCC      48
Met Ser Gly Leu Arg Asn Thr Ser Glu Ala Val Ala Val Leu Ala Ser
 1               5                  10                  15

CTG GGA CTC GGA ATG GTT CTG CTC ATG TTC GTG GCG ACG ACG CCG CCG      96
Leu Gly Leu Gly Met Val Leu Leu Met Phe Val Ala Thr Thr Pro Pro
             20                  25                  30

GCC GTT GAG GCC ACC CAG TCG GGG ATT TAC ATA GAC AAC GGC AAG GAC     144
Ala Val Glu Ala Thr Gln Ser Gly Ile Tyr Ile Asp Asn Gly Lys Asp
         35                  40                  45

CAG ACG ATC ATG CAC AGA GTG CTG AGC GAG GAC GAC AAG CTG GAC GTC     192
Gln Thr Ile Met His Arg Val Leu Ser Glu Asp Asp Lys Leu Asp Val
```

-continued

```
            50                      55                      60
TCG TAC GAG ATC CTC GAG TTC CTG GGC ATC GCC GAA CGG CCG ACG CAC       240
Ser Tyr Glu Ile Leu Glu Phe Leu Gly Ile Ala Glu Arg Pro Thr His
 65                      70                      75                  80

CTG AGC AGC CAC CAG TTG TCG CTG AGG AAG TCG GCT CCC AAG TTC CTG       288
Leu Ser Ser His Gln Leu Ser Leu Arg Lys Ser Ala Pro Lys Phe Leu
                     85                      90                      95

CTG GAC GTC TAC CAC CGC ATC ACG GCG GAG GAG GGT CTC AGC GAT CAG       336
Leu Asp Val Tyr His Arg Ile Thr Ala Glu Glu Gly Leu Ser Asp Gln
                100                     105                     110

GAT GAG GAC GAC GAC TAC GAA CGC GGC CAT CGG TCC AGG AGG AGC GCC       384
Asp Glu Asp Asp Asp Tyr Glu Arg Gly His Arg Ser Arg Arg Ser Ala
            115                     120                     125

GAC CTC GAG GAG GAT GAG GGC GAG CAG CAG AAG AAC TTC ATC ACC GAC       432
Asp Leu Glu Glu Asp Glu Gly Glu Gln Gln Lys Asn Phe Ile Thr Asp
        130                     135                     140

CTG GAC AAG CGG GCC ATC GAC GAG AGC GAC ATC ATC ATG ACC TTC CTG       480
Leu Asp Lys Arg Ala Ile Asp Glu Ser Asp Ile Ile Met Thr Phe Leu
145                     150                     155                 160

AAC AAG CGC CAC CAC AAT GTG GAC GAA CTG CGT CAC GAG CAC GGC CGT       528
Asn Lys Arg His His Asn Val Asp Glu Leu Arg His Glu His Gly Arg
                165                     170                     175

CGC CTG TGG TTC GAC GTC TCC AAC GTG CCC AAC GAC AAC TAC CTG GTG       576
Arg Leu Trp Phe Asp Val Ser Asn Val Pro Asn Asp Asn Tyr Leu Val
            180                     185                     190

ATG GCC GAG CTG CGC ATC TAT CAG AAC GCC AAC GAG GGC AAG TGG CTG       624
Met Ala Glu Leu Arg Ile Tyr Gln Asn Ala Asn Glu Gly Lys Trp Leu
        195                     200                     205

ACC GCC AAC AGG GAG TTC ACC ATC ACG GTA TAC GCC ATT GGC ACC GGC       672
Thr Ala Asn Arg Glu Phe Thr Ile Thr Val Tyr Ala Ile Gly Thr Gly
    210                     215                     220

ACG CTG GGC CAG CAC ACC ATG GAG CCG CTG TCC TCG GTG AAC ACC ACC       720
Thr Leu Gly Gln His Thr Met Glu Pro Leu Ser Ser Val Asn Thr Thr
225                     230                     235                 240

GGG GAC TAC GTG GGC TGG TTG GAG CTC AAC GTG ACC GAG GGC CTG CAC       768
Gly Asp Tyr Val Gly Trp Leu Glu Leu Asn Val Thr Glu Gly Leu His
                245                     250                     255

GAG TGG CTG GTC AAG TCG AAG GAC AAT CAT GGC ATC TAC ATT GGA GCA       816
Glu Trp Leu Val Lys Ser Lys Asp Asn His Gly Ile Tyr Ile Gly Ala
            260                     265                     270

CAC GCT GTC AAC CGA CCC GAC CGC GAG GTG AAG CTG GAC GAC ATT GGA       864
His Ala Val Asn Arg Pro Asp Arg Glu Val Lys Leu Asp Asp Ile Gly
        275                     280                     285

CTG ATC CAC CGC AAG GTG GAC GAC GAG TTC CAG CCC TTC ATG ATC GGC       912
Leu Ile His Arg Lys Val Asp Asp Glu Phe Gln Pro Phe Met Ile Gly
    290                     295                     300

TTC TTC CGC GGA CCG GAG CTG ATC AAG GCG ACG GCC CAC AGC AGC CAC       960
Phe Phe Arg Gly Pro Glu Leu Ile Lys Ala Thr Ala His Ser Ser His
305                     310                     315                 320

CAC AGG AGC AAG CGA AGC GCC AGC CAT CCA CGC AAG CGC AAG AAG TCG      1008
His Arg Ser Lys Arg Ser Ala Ser His Pro Arg Lys Arg Lys Lys Ser
                325                     330                     335

GTG TCG CCC AAC AAC GTG CCG CTG CTG GAA CCG ATG GAG AGC ACG CGC      1056
Val Ser Pro Asn Asn Val Pro Leu Leu Glu Pro Met Glu Ser Thr Arg
            340                     345                     350

AGC TGC CAG ATG CAG ACC CTG TAC ATA GAC TTC AAG GAT CTG GGC TGG      1104
Ser Cys Gln Met Gln Thr Leu Tyr Ile Asp Phe Lys Asp Leu Gly Trp
        355                     360                     365

CAT GAC TGG ATC ATC GCA CCA GAG GGC TAT GGC GCC TTC TAC TGC AGC      1152
```

```
His Asp Trp Ile Ile Ala Pro Glu Gly Tyr Gly Ala Phe Tyr Cys Ser
    370             375             380

GGC GAG TGC AAT TTC CCG CTC AAT GCG CAC ATG AAC GCC ACG AAC CAT      1200
Gly Glu Cys Asn Phe Pro Leu Asn Ala His Met Asn Ala Thr Asn His
385             390             395             400

GCG ATC GTC CAG ACC CTG GTC CAC CTG CTG GAG CCC AAG AAG GTG CCC      1248
Ala Ile Val Gln Thr Leu Val His Leu Leu Glu Pro Lys Lys Val Pro
            405             410             415

AAG CCC TGC TGC GCT CCG ACC AGG CTG GGA GCA CTA CCC GTT CTG TAC      1296
Lys Pro Cys Cys Ala Pro Thr Arg Leu Gly Ala Leu Pro Val Leu Tyr
        420             425             430

CAC CTG AAC GAC GAG AAT GTG AAC CTG AAA AAG TAT AGA AAC ATG ATT      1344
His Leu Asn Asp Glu Asn Val Asn Leu Lys Lys Tyr Arg Asn Met Ile
    435             440             445

GTG AAA TCC TGC GGG TGC CAT TGA                                       1368
Val Lys Ser Cys Gly Cys His
    450             455

(2) INFORMATION FOR SEQ ID NO:2:

(i) SEQUENCE CHARACTERISTICS:
        (A) LENGTH: 455 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Gly Leu Arg Asn Thr Ser Glu Ala Val Ala Val Leu Ala Ser
  1               5                  10                  15

Leu Gly Leu Gly Met Val Leu Leu Met Phe Val Ala Thr Thr Pro Pro
                 20                  25                  30

Ala Val Glu Ala Thr Gln Ser Gly Ile Tyr Ile Asp Asn Gly Lys Asp
             35                  40                  45

Gln Thr Ile Met His Arg Val Leu Ser Glu Asp Asp Lys Leu Asp Val
         50                  55                  60

Ser Tyr Glu Ile Leu Glu Phe Leu Gly Ile Ala Glu Arg Pro Thr His
 65                  70                  75                  80

Leu Ser Ser His Gln Leu Ser Leu Arg Lys Ser Ala Pro Lys Phe Leu
                 85                  90                  95

Leu Asp Val Tyr His Arg Ile Thr Ala Glu Glu Gly Leu Ser Asp Gln
            100                 105                 110

Asp Glu Asp Asp Asp Tyr Glu Arg Gly His Arg Ser Arg Arg Ser Ala
        115                 120                 125

Asp Leu Glu Glu Asp Glu Gly Glu Gln Gln Lys Asn Phe Ile Thr Asp
    130                 135                 140

Leu Asp Lys Arg Ala Ile Asp Glu Ser Asp Ile Ile Met Thr Phe Leu
145                 150                 155                 160

Asn Lys Arg His His Asn Val Asp Glu Leu Arg His Glu His Gly Arg
                165                 170                 175

Arg Leu Trp Phe Asp Val Ser Asn Val Pro Asn Asp Tyr Leu Val
            180                 185                 190

Met Ala Glu Leu Arg Ile Tyr Gln Asn Ala Asn Glu Gly Lys Trp Leu
        195                 200                 205

Thr Ala Asn Arg Glu Phe Thr Ile Thr Val Tyr Ala Ile Gly Thr Gly
    210                 215                 220

Thr Leu Gly Gln His Thr Met Glu Pro Leu Ser Ser Val Asn Thr Thr
225                 230                 235                 240
```

```
Gly Asp Tyr Val Gly Trp Leu Glu Leu Asn Val Thr Glu Gly Leu His
                245                 250                 255

Glu Trp Leu Val Lys Ser Lys Asp Asn His Gly Ile Tyr Ile Gly Ala
            260                 265                 270

His Ala Val Asn Arg Pro Asp Arg Glu Val Lys Leu Asp Asp Ile Gly
        275                 280                 285

Leu Ile His Arg Lys Val Asp Asp Glu Phe Gln Pro Phe Met Ile Gly
    290                 295                 300

Phe Phe Arg Gly Pro Glu Leu Ile Lys Ala Thr Ala His Ser Ser His
305                 310                 315                 320

His Arg Ser Lys Arg Ser Ala Ser His Pro Arg Lys Arg Lys Lys Ser
                325                 330                 335

Val Ser Pro Asn Asn Val Pro Leu Leu Glu Pro Met Glu Ser Thr Arg
            340                 345                 350

Ser Cys Gln Met Gln Thr Leu Tyr Ile Asp Phe Lys Asp Leu Gly Trp
        355                 360                 365

His Asp Trp Ile Ile Ala Pro Glu Gly Tyr Gly Ala Phe Tyr Cys Ser
    370                 375                 380

Gly Glu Cys Asn Phe Pro Leu Asn Ala His Met Asn Ala Thr Asn His
385                 390                 395                 400

Ala Ile Val Gln Thr Leu Val His Leu Leu Glu Pro Lys Lys Val Pro
                405                 410                 415

Lys Pro Cys Cys Ala Pro Thr Arg Leu Gly Ala Leu Pro Val Leu Tyr
            420                 425                 430

His Leu Asn Asp Glu Asn Val Asn Leu Lys Lys Tyr Arg Asn Met Ile
        435                 440                 445

Val Lys Ser Cys Gly Cys His
    450                 455

(2) INFORMATION FOR SEQ ID NO:3:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
         (A) ORGANISM: Homo sapiens
         (F) TISSUE TYPE: HIPPOCAMPUS (ix) FEATURE:
         (A) NAME/KEY: Protein
         (B) LOCATION: 1..139
         (D) OTHER INFORMATION: /label= hOP1-MATURE (xi) SEQUENCE DESCRIPTION: SEQ ID NO:3:

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80
```

```
Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Asn Val Ile Leu Lys Lys Tyr
        115                 120                 125

Arg Asn Met Val Val Arg Ala Cys Gly Cys His
    130                 135
```

(2) INFORMATION FOR SEQ ID NO:4:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: MURIDAE
        (F) TISSUE TYPE: EMBRYO (ix) FEATURE:
        (A) NAME/KEY: Protein
        (B) LOCATION: 1..139
        (D) OTHER INFORMATION: /label= MOP1-MATURE (xi) SEQUENCE DESCRIPTION: SEQ ID NO:4:

```
Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Asp Thr Val Pro Lys Pro Cys Cys Ala Pro Thr Gln Leu Asn Ala Ile
            100                 105                 110

Ser Val Leu Tyr Phe Asp Asp Ser Asn Val Ile Leu Lys Lys Tyr
        115                 120                 125

Arg Asn Met Val Val Arg Ala Cys Gly Cys His
    130                 135
```

(2) INFORMATION FOR SEQ ID NO:5:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS
        (F) TISSUE TYPE: HIPPOCAMPUS (ix) FEATURE:
        (A) NAME/KEY: Protein (B) LOCATION: 1..139
                (D) OTHER INFORMATION: /label= HOP2-MATURE (xi) SEQUENCE DESCRIPTION: SEQ ID NO:5:

Ala Val Arg Pro Leu Arg Arg Gln Pro Lys Lys Ser Asn Glu Leu
1               5                   10                  15

Pro Gln Ala Asn Arg Leu Pro Gly Ile Phe Asp Asp Val His Gly Ser
            20                  25                  30

His Gly Arg Gln Val Cys Arg Arg His Glu Leu Tyr Val Ser Phe Gln
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ser Phe Pro Leu Asp Ser Cys Met Asn
65              70                  75                  80

Ala Thr Asn His Ala Ile Leu Gln Ser Leu Val His Leu Met Lys Pro
                85                  90                  95

Asn Ala Val Pro Lys Ala Cys Cys Ala Pro Thr Lys Leu Ser Ala Thr
            100                 105                 110

Ser Val Leu Tyr Tyr Asp Ser Ser Asn Val Ile Leu Arg Lys His
        115                 120                 125

Arg Asn Met Val Val Lys Ala Cys Gly Cys His
    130                 135

(2) INFORMATION FOR SEQ ID NO:6:

(i) SEQUENCE CHARACTERISTICS:
                (A) LENGTH: 139 amino acids
                (B) TYPE: amino acid
                (C) STRANDEDNESS: single
                (D) TOPOLOGY: linear (ii) MOLECULE TYPE: protein (vi) ORIGINAL SOURCE:
                (A) ORGANISM: MURIDAE
                (F) TISSUE TYPE: EMBRYO (ix) FEATURE:
                (A) NAME/KEY: Protein
                (B) LOCATION: 1..139
                (D) OTHER INFORMATION: /label= MOP2-MATURE (xi) SEQUENCE DESCRIPTION: SEQ ID NO:6:

Ala Ala Arg Pro Leu Lys Arg Arg Gln Pro Lys Lys Thr Asn Glu Leu
1               5                   10                  15

Pro His Pro Asn Lys Leu Pro Gly Ile Phe Asp Asp Gly His Gly Ser
            20                  25                  30

Arg Gly Arg Glu Val Cys Arg Arg His Glu Leu Tyr Val Ser Phe Arg
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ala Phe Pro Leu Asp Ser Cys Met Asn
65              70                  75                  80

Ala Thr Asn His Ala Ile Leu Gln Ser Leu Val His Leu Met Lys Pro
                85                  90                  95

Asp Val Val Pro Lys Ala Cys Cys Ala Pro Thr Lys Leu Ser Ala Thr
            100                 105                 110

Ser Val Leu Tyr Tyr Asp Ser Ser Asn Val Ile Leu Arg Lys His
        115                 120                 125

Arg Asn Met Val Val Lys Ala Cys Gly Cys His

```
        130             135

(2) INFORMATION FOR SEQ ID NO:7:

(i) SEQUENCE CHARACTERISTICS:
         (A) LENGTH: 101 amino acids
         (B) TYPE: amino acid
         (C) STRANDEDNESS: single
         (D) TOPOLOGY: linear (ii) MOLECULE TYPE: protein (vi) ORIGINAL SOURCE:
         (A) ORGANISM: bovinae (ix) FEATURE:
         (A) NAME/KEY: Protein
         (B) LOCATION: 1..101
         (D) OTHER INFORMATION: /label= CBMP-2A-FX (xi) SEQUENCE DESCRIPTION: SEQ ID NO:7:

Cys Lys Arg His Pro Leu Tyr Val Asp Phe Ser Asp Val Gly Trp Asn
1               5                  10                  15

Asp Trp Ile Val Ala Pro Pro Gly Tyr His Ala Phe Tyr Cys His Gly
            20                  25                  30

Glu Cys Pro Phe Pro Leu Ala Asp His Leu Asn Ser Thr Asn His Ala
        35                  40                  45

Ile Val Gln Thr Leu Val Asn Ser Val Asn Ser Lys Ile Pro Lys Ala
    50                  55                  60

Cys Cys Val Pro Thr Glu Leu Ser Ala Ile Ser Met Leu Tyr Leu Asp
65                  70                  75                  80

Glu Asn Glu Lys Val Val Leu Lys Asn Tyr Gln Asp Met Val Val Glu
                85                  90                  95

Gly Cys Gly Cys Arg
            100

(2) INFORMATION FOR SEQ ID NO:8:

(i) SEQUENCE CHARACTERISTICS:
         (A) LENGTH: 101 amino acids
         (B) TYPE: amino acid
         (C) STRANDEDNESS: single
         (D) TOPOLOGY: linear (ii) MOLECULE TYPE: protein (vi) ORIGINAL SOURCE:
         (A) ORGANISM: HOMO SAPIENS
         (F) TISSUE TYPE: hippocampus (ix) FEATURE:
         (A) NAME/KEY: Protein
         (B) LOCATION: 1..101
         (D) OTHER INFORMATION: /label= CBMP-2B-FX (xi) SEQUENCE DESCRIPTION: SEQ ID NO:8:

Cys Arg Arg His Ser Leu Tyr Val Asp Phe Ser Asp Val Gly Trp Asn
1               5                  10                  15

Asp Trp Ile Val Ala Pro Pro Gly Tyr Gln Ala Phe Tyr Cys His Gly
            20                  25                  30

Asp Cys Pro Phe Pro Leu Ala Asp His Leu Asn Ser Thr Asn His Ala
        35                  40                  45

Ile Val Gln Thr Leu Val Asn Ser Val Asn Ser Ser Ile Pro Lys Ala
    50                  55                  60

Cys Cys Val Pro Thr Glu Leu Ser Ala Ile Ser Met Leu Tyr Leu Asp
```

```
                65                  70                  75                  80
Glu Tyr Asp Lys Val Val Leu Lys Asn Tyr Gln Glu Met Val Val Glu
                        85                  90                  95
Gly Cys Gly Cys Arg
            100
```

(2) INFORMATION FOR SEQ ID NO:9:

(i) SEQUENCE CHARACTERISTICS:
    (A) LENGTH: 102 amino acids
    (B) TYPE: amino acid
    (C) STRANDEDNESS: single
    (D) TOPOLOGY: linear (ii) MOLECULE TYPE: protein (vi) ORIGINAL SOURCE:
    (A) ORGANISM: DROSOPHILA MELANOGASTER (ix) FEATURE:
    (A) NAME/KEY: Protein
    (B) LOCATION: 1..102
    (D) OTHER INFORMATION: /label= DPP-FX (xi) SEQUENCE DESCRIPTION: SEQ ID NO:9:

```
Cys Arg Arg His Ser Leu Tyr Val Asp Phe Ser Asp Val Gly Trp Asp
1               5                   10                  15
Asp Trp Ile Val Ala Pro Leu Gly Tyr Asp Ala Tyr Tyr Cys His Gly
                20                  25                  30
Lys Cys Pro Phe Pro Leu Ala Asp His Phe Asn Ser Thr Asn His Ala
                35                  40                  45
Val Val Gln Thr Leu Val Asn Asn Asn Pro Gly Lys Val Pro Lys
 50                  55                  60
Ala Cys Cys Val Pro Thr Gln Leu Asp Ser Val Ala Met Leu Tyr Leu
65                  70                  75                  80
Asn Asp Gln Ser Thr Val Val Leu Lys Asn Tyr Gln Glu Met Thr Val
                        85                  90                  95
Val Gly Cys Gly Cys Arg
                100
```

(2) INFORMATION FOR SEQ ID NO:10:

(i) SEQUENCE CHARACTERISTICS:
    (A) LENGTH: 102 amino acids
    (B) TYPE: amino acid
    (C) STRANDEDNESS: single
    (D) TOPOLOGY: linear (ii) MOLECULE TYPE: protein (vi) ORIGINAL SOURCE:
    (A) ORGANISM: XENOPUS (ix) FEATURE:
    (A) NAME/KEY: Protein
    (B) LOCATION: 1..102
    (D) OTHER INFORMATION: /label= VGL-FX (xi) SEQUENCE DESCRIPTION: SEQ ID NO:10:

```
Cys Lys Lys Arg His Leu Tyr Val Glu Phe Lys Asp Val Gly Trp Gln
1               5                   10                  15
Asn Trp Val Ile Ala Pro Gln Gly Tyr Met Ala Asn Tyr Cys Tyr Gly
                20                  25                  30
Glu Cys Pro Tyr Pro Leu Thr Glu Ile Leu Asn Gly Ser Asn His Ala
                35                  40                  45
```

```
Ile Leu Gln Thr Leu Val His Ser Ile Glu Pro Glu Asp Ile Pro Leu
    50                  55                  60
Pro Cys Cys Val Pro Thr Lys Met Ser Pro Ile Ser Met Leu Phe Tyr
65                   70                  75                  80
Asp Asn Asn Asp Asn Val Val Leu Arg His Tyr Glu Asn Met Ala Val
                85                  90                  95
Asp Glu Cys Gly Cys Arg
            100
```

(2) INFORMATION FOR SEQ ID NO:11:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: MURIDAE (ix) FEATURE:
        (A) NAME/KEY: Protein
        (B) LOCATION: 1..102
        (D) OTHER INFORMATION: /label= VGR-1-FX (xi) SEQUENCE DESCRIPTION: SEQ ID NO:11:

```
Cys Lys Lys His Glu Leu Tyr Val Ser Phe Gln Asp Val Gly Trp Gln
1               5                   10                  15
Asp Trp Ile Ile Ala Pro Lys Gly Tyr Ala Ala Asn Tyr Cys Asp Gly
            20                  25                  30
Glu Cys Ser Phe Pro Leu Asn Ala His Met Asn Ala Thr Asn His Ala
        35                  40                  45
Ile Val Gln Thr Leu Val His Val Met Asn Pro Glu Tyr Val Pro Lys
    50                  55                  60
Pro Cys Cys Ala Pro Thr Lys Val Asn Ala Ile Ser Val Leu Tyr Phe
65                  70                  75                  80
Asp Asp Asn Ser Asn Val Ile Leu Lys Lys Tyr Arg Asn Met Val Val
                85                  90                  95
Arg Ala Cys Gly Cys His
            100
```

(2) INFORMATION FOR SEQ ID NO:12:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens
        (F) TISSUE TYPE: brain (ix) FEATURE:
        (A) NAME/KEY: Protein
        (B) LOCATION: 1..106
        (D) OTHER INFORMATION: /note= "GDF-1 (fx)"

(xi) SEQUENCE DESCRIPTION: SEQ ID NO:12:

```
Cys Arg Ala Arg Arg Leu Tyr Val Ser Phe Arg Glu Val Gly Trp His
1               5                   10                  15
```

```
Arg Trp Val Ile Ala Pro Arg Gly Phe Leu Ala Asn Tyr Cys Gln Gly
             20                  25                  30

Gln Cys Ala Leu Pro Val Ala Leu Ser Gly Ser Gly Gly Pro Pro Ala
         35                  40                  45

Leu Asn His Ala Val Leu Arg Ala Leu Met His Ala Ala Pro Gly
     50                  55                  60

Ala Ala Asp Leu Pro Cys Cys Val Pro Ala Arg Leu Ser Pro Ile Ser
 65              70                  75                  80

Val Leu Phe Phe Asp Asn Ser Asp Asn Val Val Leu Arg Gln Tyr Glu
                 85                  90                  95

Asp Met Val Val Asp Glu Cys Gly Cys Arg
             100                 105
```

(2) INFORMATION FOR SEQ ID NO:13:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..104
        (D) OTHER INFORMATION: /note= "BMP3"

(xi) SEQUENCE DESCRIPTION: SEQ ID NO:13:

```
Cys Ala Arg Arg Tyr Leu Lys Val Asp Phe Ala Asp Ile Gly Trp Ser
 1               5                  10                  15

Glu Trp Ile Ile Ser Pro Lys Ser Phe Asp Ala Tyr Tyr Cys Ser Gly
             20                  25                  30

Ala Cys Gln Phe Pro Met Pro Lys Ser Leu Lys Pro Ser Asn His Ala
         35                  40                  45

Thr Ile Gln Ser Ile Val Ala Arg Ala Val Gly Val Val Pro Gly Ile
     50                  55                  60

Pro Glu Pro Cys Cys Val Pro Glu Lys Met Ser Ser Leu Ser Ile Leu
 65              70                  75                  80

Phe Phe Asp Glu Asn Lys Asn Val Val Leu Lys Val Tyr Pro Asn Met
                 85                  90                  95

Thr Val Glu Ser Cys Ala Cys Arg
                 100
```

(2) INFORMATION FOR SEQ ID NO:14:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS (ix) FEATURE:
        (A) NAME/KEY: Protein
        (B) LOCATION: 1..102
        (D) OTHER INFORMATION: /note= "BMP5"

(xi) SEQUENCE DESCRIPTION: SEQ ID NO:14:

```
Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Phe Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Leu Met Phe Pro Asp His Val Pro Lys
    50                  55                  60

Pro Cys Cys Ala Pro Thr Lys Leu Asn Ala Ile Ser Val Leu Tyr Phe
65              70                  75                  80

Asp Asp Ser Ser Asn Val Ile Leu Lys Lys Tyr Arg Asn Met Val Val
                85                  90                  95

Arg Ser Cys Gly Cys His
                100
```

(2) INFORMATION FOR SEQ ID NO:15:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS (ix) FEATURE:
        (A) NAME/KEY: Protein
        (B) LOCATION: 1..102
        (D) OTHER INFORMATION: /note= "BMP6"

(xi) SEQUENCE DESCRIPTION: SEQ ID NO:15:

```
Cys Arg Lys His Glu Leu Tyr Val Ser Phe Gln Asp Leu Gly Trp Gln
1               5                   10                  15

Asp Trp Ile Ile Ala Pro Lys Gly Tyr Ala Ala Asn Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Leu Met Asn Pro Glu Tyr Val Pro Lys
    50                  55                  60

Pro Cys Cys Ala Pro Thr Lys Leu Asn Ala Ile Ser Val Leu Tyr Phe
65              70                  75                  80

Asp Asp Asn Ser Asn Val Ile Leu Lys Lys Tyr Arg Trp Met Val Val
                85                  90                  95

Arg Ala Cys Gly Cys His
                100
```

(2) INFORMATION FOR SEQ ID NO:16:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:16:

Arg Xaa Xaa Arg

60A PROTEIN-INDUCED MORPHOGENESIS

REFERENCE TO RELATED APPLICATIONS

This is a continuation of Ser. No. 07/945,292 filed on Sep. 15, 1992 now abandoned, which is a continuation-in-part of the U.S. application Ser. Nos.: 1) U.S. Ser. No. 07/922,813, filed Jul. 31, 1992, now abandoned, which is a continuation-in-part of U.S. Ser. No. 07/752,764, filed Aug. 30, 1991, now abandoned, which is a continuation-in-part of U.S. Ser. No. 07/667,274, filed Mar. 11, 1991, now abandoned; 2) U.S. Ser. No. 07/923,780, filed Jul. 31, 1992, now abandoned, which is a continuation-in-part of U.S. Ser. No. 07/752,764 and U.S. Ser. No. 07/752,857, both filed Aug. 30, 1991, both now abandoned, and both continuations-in-part of Ser. No. 07/667,274; and 3) U.S. Ser. No. 07/753,059, filed Aug. 30, 1991, now abandoned, which is a continuation-in-part of Ser. No. 07/667,274. The disclosures of these applications are incorporated by reference herein.

BACKGROUND OF THE INVENTION

This invention relates to methods for the use of morphogenically active fragments of 60A protein to induce tissue morphogenesis in mammals, including methods for promoting tissue stasis, repair and regeneration, and methods for increasing progenitor cell populations using morphogenically active fragments of the protein.

Cell differentiation is the central characteristic of morphogenesis which initiates in the embryo, and continues to various degrees throughout the life of an organism in adult tissue repair and regeneration mechanisms. The degree of morphogenesis in adult tissue varies among different tissues and is related, among other things, to the degree of cell turnover in a given tissue. On this basis, tissues can be divided into three broad categories: (1) tissues with static cell populations such as nerve and skeletal muscle where there is no cell division and most of the cells formed during early development persist throughout adult life; (2) tissues containing conditionally renewing populations such as liver where there is generally little cell division but, in response to an appropriate stimulus, cells can divide to produce daughters of the same differentially defined type; and (3) tissues with permanently renewing populations including blood, testes and stratified squamous epithelia which are characterized by rapid and continuous cell turnover in the adult. Here, the terminally differentiated cells have a relatively short life span and are replaced through proliferation of a distinct subpopulation of cells, known as stem or progenitor cells.

The cellular and molecular events which govern the stimulus for differentiation of these cells is an area of intensive research. In the medical field, it is anticipated that the discovery of factor(s) which control cell differentiation and tissue morphogenesis will advance significantly medicine's ability to repair and regenerate diseased or damaged mammalian tissues and organs. Particularly useful areas include reconstructive surgery and in the treatment of tissue degenerative diseases including arthritis, emphysema, osteoporosis, cardiomyopathy, cirrhosis, and degenerative nerve diseases.

A number of different factors have been isolated in recent years which appear to play a role in cell differentiation.

Recently, various members of the structurally related proteins of the transforming growth factor (TGF)-β superfamily of proteins have been identified as true morphogens. This "family" of proteins, sharing substantial amino acid sequence homology within their morphogenically active C-terminal domains, including a conserved six or seven cysteine skeleton, are capable of inducing tissue-specific morphogenesis in a variety of organs and tissues, including bone, cartilage, liver, dentin, periodontal ligament, cementum, nerve tissue and the epithelial mucosa of the gastrointestinal tract (see the copending, related U.S. applications Ser. No. 667,274, filed Mar. 11, 1991 abandoned in favor of (U.S. application Ser. No. 08/404,113 filed, Mar. 14, 1995) and U.S. application Ser. No. 08/404,113 filed Mar. 14, 1995 and U.S. application Ser. No. 08/260,675, filed Jun. 16, 1994 and U.S. application Ser. No. 08/132,883 filed May 21, 1995. The proteins apparently bind to surface receptors or otherwise contact and interact with progenitor cells, predisposing or stimulating the cells to proliferate and differentiate in a morphogenically permissive environment. The morphogens are capable of inducing the developmental cascade of cellular and molecular events that culminate in the formation of new organ-specific tissue, including any vascularization, connective tissue formation, and nerve ennervation as required by the naturally occurring tissue.

Among the proteins useful in tissue morphogenesis are proteins originally identified as bone inductive proteins, such as the OP-1 (comprising, e.g. Seq. ID NO. 3), OP-2 (comprising, e.g. Seq. ID NO. 5) and the CBMP2 (comprising, e.g. Seq. ID NO. 7 and 8) proteins, as well as amino acid sequence-related proteins such as BMP5 (comprising, e.g., Seq. ID NO. 14) and BMP6 (comprising, e.g., Seq. ID NO. 15), DPP (comprising, e.g., Seq. ID NO. 9) (from Drosophila), Vgl (comprising, e.g., Seq. ID NO. 10) (from Xenopus), and Vgr-1 (comprising, e.g., Seq. ID NO. 11) and GDF-1 (comprising, e.g., Seq. ID NO. 12) (from mouse see, for example, application Ser. No. 08/404, 113, filed Mar. 14, 1995, U.S. Ser. No. 667,274 (abandoned in favor of CIP U.S. application Ser. No. 08/404,113, filed Mar. 14, 1995 and application Ser. No. 08/432,883 filed May 2, 1995. These TGF-β superfamily members comprise a distinct subfamily of proteins different from other members of the TGF-β superfamily in that the family of morphogenic proteins are able to induce the full cascade of events that result in tissue morphogenesis, including stimulating cell proliferation and cell differentiation, supporting the growth and maintenance of differentiated cells and inducing the "redifferentiation" of transformed cells to display a morphology characteristic of untransformed cells. The morphogenic proteins apparently act as endocrine factors rather than as local-acting growth factors like TGF-β. Specifically, the endogenous morphogens may be synthesized and secreted from a factor-producing tissue and can be transported to, and act on, a tissue at a distance, e.g., a tissue other than the tissue in which they are synthesized.

The morphogens are synthesized in the cell as a precursor molecule approximately three times larger than the mature protein that is processed to yield mature disulfide-linked dimers comprising the C-terminal domain of the precursor sequence. The proteins are inactive when reduced, but are active as oxidized homodimeric species as well as when oxidized in combination with other morphogens to produce heterodimers. The proteins useful in tissue morphogenesis typically require a suitable environment enabling cells to proliferate and differentiate in a tissue-specific manner into, e.g., bone-producing osteoblasts, hemopoietic cells, or liver cells, depending on the nature of the local environment. The proliferation and differentiation of cells induced by the morphogenic proteins requires a suitable local environment including a suitable substratum on which the cells can anchor. The proliferating and differentiating cells also require the presence of appropriate signals to direct their tissue-specificity, such as cell surface markers.

Recently, another member of the TFG-β superfamily of structurally related proteins has been identified in Drosophila melanogaster, the Drosophila 60A gene (comprising, e.g., Seq. ID NO. 1) (Wharton et al., (1991) *Proc. Nat'l. Acad. Sci. USA* 88: 9214–9218.) Northern blot analysis of Drosophila tissue with a C-terminal 60A-specific probe suggests that the 60A gene (comprising, e.g., Seq. ID NO. 1) is expressed throughout development with peaks of transcription during early embryogenesis. The 60A gene (comprising, e.g., Seq. ID NO. 1) consists of a single exon comprising a 1365 base-pair open reading frame encoding a 455 amino acid protein. It has been discovered that the encoded amino acid sequence for 60A (comprising, e.g., Seq. ID NO. 2) includes regions sharing high sequence homology with members of the family of morphogenic proteins.

It is an object of this invention to provide methods for utilizing a morphogenically active fragment of the 60A protein (comprising, e.g., Seq. ID NO. 2) to induce the developmental cascade of tissue morphogenesis for a variety of tissues in mammals. The morphogenic properties of 60A protein (comprising, e.g., Seq. ID NO. 2) include the ability to induce proliferation and differentiation of progenitor cells, and the ability to support and maintain the differentiated phenotype through the progression of events that results in the formation of adult tissue. Another object is to provide methods for the expression and isolation of a morphogenically active fragment of 60A protein (comprising, e.g., Seq. ID NO. 2) using recombinant DNA techniques. Still another object is to provide tissue-specific acellular matrices that may be used in combination with a morphogenically active fragment of 60A protein (comprising, e.g., Seq. ID NO. 2), and methods for their production. Other objects include utilizing a morphogenically active fragment of 60A protein (comprising, e.g., Seq. ID NO. 2) in a range of methods, including methods for increasing a progenitor cell population in a mammal; methods for stimulating progenitor cells to differentiate in vivo or in vitro and to maintain their differentiated phenotype; methods for inducing tissue-specific growth in vivo, and methods for the replacement of diseased or damaged tissue in vivo. These and other objects and features of the invention will be apparent from the description, drawings, and claims which follow.

SUMMARY OF THE INVENTION

This invention provides methods for utilizing morphogenically active fragments of 60A protein (comprising, e.g., Seq. ID NO. 2) to induce the developmental cascade of tissue morphogenesis in a mammal. Specifically, methods are provided for utilizing a morphogenically active fragment of 60A protein (comprising, e.g., Seq. ID NO. 2) to induce the proliferation of uncommitted progenitor cells, to induce the differentiation of these stimulated progenitor cells in a tissue-specific manner under appropriate environmental conditions, and to support the growth and maintenance of these differentiated cells. The protein also may be used to stimulate the "redifferentiation" of cells induced to stray from their differentiated phenotypes. Accordingly, 60A protein (comprising, e.g., Seq. ID NO. 2) can be utilized to initiate and maintain the developmental cascade of tissue morphogenesis in an appropriate, morphogenically permissive environment.

As used herein, useful Protein 60A morphogens include proteins encoded by the DNA sequence provided in Seq. ID No. 1 and allelic variants thereof, as well as other naturally-occurring and biosynthetic mutants that are morphogenically active as defined herein. "Morphogenically active fragments" is understood to include all proteins and protein fragments encoded by part or all of the sequence of Seq. ID No. 1, and which have morphogenic activity as defined herein. Specifically, as defined herein, a morphogen is a dimeric protein comprising a pair of polypeptide chains, wherein each polypeptide chain comprises at least the C-terminal six cysteine skeleton defined by residues 359–455 of Seq. ID No. 1 (or residues 43–139 of Seq. ID No. 3), including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is capable of acting as a morphogen as defined herein. Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. In addition, it is also anticipated that these morphogens are capable of inducing redifferentiation of committed cells under appropriate environmental conditions.

In one aspect, the morphogens of this invention comprise a morphogenically active dimeric species comprising a pair of polypeptide chains, wherein at least one of the polypeptide chains comprises the amino acid sequence defined by residues 359–455 of Seq. ID No. 1, including allelic and other mutant variants thereof. In preferred morphogens, at least one polypeptide chain comprises the sequence defined by residues 354–455 or residues 326–455 of Seq. ID No. 1. Alternatively, the amino acid sequence of both polypeptide chains may be defined by part or all of the amino acid sequence of Seq. ID NO. 1, including allelic and other mutant variants thereof. Where only one polypeptide chain is defined by the amino acid sequence of part or all of Seq. ID. No. 1, the other polypeptide chain preferably comprises at least the sequence defining the C-terminal six cysteine skeleton of any of the other known morphogen family members, including OP1, OP2, CBMP2A, CBMP2B, BMP3, BMP6, Vgl, Vgr-1, DPP and GDF-1, (described in Seq. ID. Nos. 3, 5, 7, 8, 13, 15, 10, 11, 9, and 12, respectively), including allelic, species and other mutant variants thereof. Other useful sequences include biosynthetic constructs, such as are described in U.S. Pat. No. 5,011,691.

In one aspect of the invention, morphogenic 60A proteins (comprising, e.g., Seq. ID NO. 2) are useful in the replacement of diseased or damaged tissue in a mammal, such as damaged lung tissue resulting from emphysema; cirrhotic kidney or liver tissue; damaged heart or blood vessel tissue, as may result from cardiomyopathies and/or atherothrombotic or cardioembolic strokes; damaged stomach and other tissues of the gastrointestinal tract resulting from ulceric perforations or their repair; damaged nerve tissue as may result from physical injury, degenerative diseases such as Alzheimer's disease or multiple sclerosis, or strokes; damaged bone tissue as may result from metabolic bone diseases and other bone remodeling disorders; or damaged dentin, periodontal and/or cementum tissue as may result from disease or mechanical injury.

As provided herein, morphogenically active fragments of 60A protein (comprising, e.g., Seq. ID NO. 2) are provided to a tissue-specific locus in vivo, to induce the developmental cascade of tissue morphogenesis at that site. Cells stimulated ex vivo by contact with 60A protein (comprising, e.g., Seq. ID NO. 2) also may be provided to the tissue locus. In these cases the existing tissue provides the necessary matrix requirements, providing a suitable substratum for the proliferating and differentiating cells in a morphogenically permissive environment, as well as providing the necessary signals for directing the tissue-specificity of the developing tissue. Alternatively, the proteins or stimulated cells may be combined with a formulated matrix and implanted as a device at a locus in vivo. The formulated matrix should be a biocompatible, preferably biodegradable, appropriately modified tissue-specific acellular matrix having the characteristics described below.

In many instances, the loss of tissue function results from the tissue destructive effects and the subsequent formation of scar tissue associated with the body's immune/inflammatory response to an initial or repeated injury to the tissue. The degree of scar tissue formation generally depends on the regenerative properties of the injured tissue, and on the degree and type of tissue damage. Thus, in another aspect, morphogenically active fragments of 60A protein (comprising, e.g., Seq. ID NO. 2) may be used to prevent or to substantially inhibit the formation of scar tissue, including alleviating immune response-mediated tissue damage, by providing morphogenic 60A protein (comprising, e.g., Seq. ID NO. 2) or cells stimulated by the 60A protein (comprising, e.g., Seq. ID NO. 2), to a newly injured tissue locus. The protein also may be provided as a prophylactic, provided to a site in anticipation of tissue injury, such as part of a surgical or other clinical procedure likely to produce tissue damage, and to induce an inflammatory/immune response.

60A protein (comprising, e.g., Seq. ID NO. 2) also may be used to increase or regenerate a progenitor or stem cell population in a mammal. For example, progenitor cells may be isolated from an individual's bone marrow, stimulated ex vivo with morphogenic 60A protein (comprising, e.g., Seq. ID NO. 2) for a time and at a concentration sufficient to induce the cells to proliferate, and returned to the bone marrow. Other sources of progenitor cells that may be suitable include biocompatible cells obtained from a cultured cell line, stimulated in culture, and subsequently provided to the body. Alternatively, 60A protein (comprising, e.g., Seq. ID NO. 2) may be provided by systemic (e.g., oral or parenteral) administration, or it may be injected or otherwise provided to a progenitor cell population in an individual to induce its mitogenic activity in vivo. For example, a morphogenically active fragment of 60A protein (comprising, e.g., Seq. ID NO. 2) may be provided to the cells in vivo, e.g., by systemic injection, to induce mitogenic activity. Similarly, a particular population of hemopoietic stem cells may be increased by exposure to 60A protein (comprising, e.g., Seq. ID NO. 2), for example by plasmaphoresis of an individual's blood to extract the cells of interest, stimulating these cells ex vivo, and returning the stimulated cells to the blood.

It is anticipated that the ability to augment an individual's progenitor cell population will enhance significantly existing methods for treating disorders resulting from a loss or reduction of a renewable cell population. Two particularly significant applications include the treatment of blood disorders and diseases involving impaired or lost immune function. Other cell populations whose proliferation may be exploited include the stem cells of the epidermis, which may be used in skin tissue regeneration, and the stem cells of the gastrointestinal lining, such as, for example, in the healing of ulcers, including gastric ulcers, and the ulcerations induced in oral mucocitis and inflammatory bowel disease.

In another aspect of the invention, morphogenic 60A protein (comprising, e.g., Seq. ID NO. 2) may be used to support the growth and maintenance of differentiated cells, inducing existing differentiated cells to continue expressing their phenotype. It is anticipated that this activity will be particularly useful in the treatment of tissue disorders where loss of function is caused by reduced or lost metabolic function and cells become senescent or quiescent, such as may occur in aging cells and/or may be manifested in osteoporosis and a number of nerve degenerative diseases, including Alzheimer's disease. Application of 60A protein (comprising, e.g., Seq. ID NO. 2) directly to the cells to be treated, or providing it systemically, as by oral or parenteral administration, can stimulate these cells to continue expressing their phenotype, thereby significantly reversing the effects of the dysfunction. In addition, a morphogenically active fragment of 60A protein (comprising, e.g., Seq. ID NO. 2) also may be used in gene therapy protocols to stimulate the growth of quiescent cells, thereby potentially enhancing the ability of these cells to incorporate exogenous DNA.

In yet another aspect of the invention, a morphogenically active fragment of 60A protein (comprising, e.g., Seq. ID NO. 2) also may be used to induce "redifferentiation" of cells that have strayed from their differentiation pathway, such as can occur during tumorgenesis. It is anticipated that this activity will be particularly useful in treatments to reduce or substantially inhibit the growth of neoplasms. The method also is anticipated to induce the de- and re-differentiation of these cells. As described supra, a morphogenic 60A protein (comprising, e.g., Seq. ID NO. 2) fragment may be provided to the cells directly or systemically.

In still another aspect of the invention, 60A protein (comprising, e.g., Seq. ID NO. 2) may be used to stimulate cell adhesion molecule (CAM) expression levels in a cell. CAMs are molecules defined as carrying out cell-cell interactions necessary for tissue formation. CAMs are believed to play a fundamental regulatory role in tissue development, including tissue boundary formation, embryonic induction and migration, and tissue stabilization and regeneration. Altered CAM levels have been implicated in a number of tissue disorders, including congenital defects, neoplasias, and degenerative diseases.

In particular, N-CAM expression is associated with normal neuronal cell development and differentiation, including retinal formation, synaptogenesis, and nerve-muscle tissue adhesion. Inhibition of one or more of the N-CAM isoforms is known to prevent proper tissue development. Altered N-CAM expression levels also are associated with neoplasias, including neuroblastomas (see infra), as well as with a number of neuropathies, including normal pressure hydrocephalous and type II schizophrenia. Application of the morphogen directly to the cells to be treated, or providing the morphogen to the mammal systemically, for example, parenterally, or indirectly by oral administration, may be used to induce cellular expression of one or more CAMs, particularly N-CAMs and L1.

CAMs also have been postulated as part of a morphoregulatory pathway whose activity is induced by a to date unidentified molecule (See, for example, Edelman, G. M. (1986) *Ann. Rev. Cell Biol.* 2:81–116). Without being limited to any given theory, the morphogens described herein may act as the inducer of this pathway.

The matrices utilized in the methods of the invention may be derived from organ-specific tissue, or they may be formulated synthetically. In one embodiment of the invention, when 60A protein (comprising, e.g., Seq. ID NO. 2) (or a collection of progenitor cells stimulated by 60A protein (comprising, e.g., Seq. ID NO. 2)) is provided at a tissue-specific locus, e.g., by systemic administration, implantation or injection at a tissue-specific locus, the existing tissue at that locus, whether diseased or damaged, has the capacity of acting as a suitable matrix. Alternatively, a formulated matrix may be provided externally together with the stimulated progenitor cells or morphogenically active 60A protein (comprising, e.g., Seq. ID NO. 2) fragment, as may be necessary when the extent of injury sustained by the damaged tissue is large. The matrix should be a biocompatible, suitably modified acellular matrix having dimensions such that it allows the influx, differentiation, and proliferation of migratory progenitor cells, and is capable of providing a morphogenically permissive environment. The matrix also preferably is tissue-specific, and biodegradable.

Formulated matrices may be generated from dehydrated organ-specific tissue, prepared for example, by treating the tissue with solvents to substantially remove the intracellular, non-structural components from the tissue. Alternatively, the matrix may be formulated synthetically using a biocompatible, preferably in vivo biodegradable, structural molecule in association with suitable tissue-specific cell attachment factors. The molecule may be a naturally occurring one such as collagen, laminin or hyaluronic acid, or a synthetic polymer comprising, for example, polylactic acid, polybutyric acid, polyglycolic acid, and copolymers thereof. Currently preferred structural polymers comprise tissue-specific collagens. Currently preferred cell attachment factors include glycosaminoglycans and proteoglycans. The matrix further may be treated with an agent or agents to increase the number of pores and micropits on its surfaces, so as to enhance the influx, proliferation and differentiation of migratory progenitor cells from the body of the mammal.

The invention thus relates to compositions and methods for the use of morphogenically active fragments of 60A protein, a species variant of the generic family of morphogens disclosed in U.S. Ser. No. 667,274 (abandoned in favor of CIP U.S. application Ser. No. 08/404,113, filed Mar. 14, 1995) and U.S. Ser. No. 752,764, (application Ser. No. 08/404,113, filed Mar. 14, 1995) as a tissue morphogen. Morphogenically active 60A proteins (comprising, e.g., Seq. ID NO. 2) and protein fragments can be isolated from naturally-occurring sources, or they may be constructed biosynthetically using conventional recombinant DNA technology. Active 60A protein (comprising, e.g., Seq. ID NO. 2) useful in the compositions and methods of this invention may include forms having varying glycosylation patterns, varying N-termini and active truncated forms, e.g., produced by recombinant DNA techniques. The 60A proteins (comprising, e.g., Seq. ID NO. 2) can be expressed from intact or truncated cDNA or from synthetic DNAs in procaryotic or eucaryotic host cells, and purified, cleaved, refolded, and dimerized to form morphogenically active compositions. Useful host cells include procaryotes, including *E. coli*, and eucaryotic cells, including mammalian cells, such as CHO, COS or BSC cells, or the insect/baculovirus system. Thus recombinant DNA techniques may be utilized to produce large quantities of 60A protein (comprising, e.g., Seq. ID NO. 2) capable of inducing tissue-specific cell differentiation and tissue morphogenesis in a variety of mammals, including humans.

DETAILED DESCRIPTION

The invention provides methods and compositions for inducing the developmental cascade of tissue morphogenesis in a mammal utilizing morphogenically active fragments of the *Drosophila melanogaster* 60A protein (comprising, e.g., Seq. ID NO. 2). The methods and compositions provided herein may be utilized in a range of applications, including stimulating the proliferation and/or differentiation of progenitor cells and inducing the repair and regeneration of damaged tissue. The morphogenic 60A proteins (comprising, e.g., Seq. ID NO. 2) of the invention are a species variant of the family of morphogens disclosed in copending U.S. Ser. No. 667,274, U.S. Ser. No. 752,764, (abandoned in favor of CIP U.S. application Ser. No. 08/404, 113, filed Mar. 14, 1995) application Ser. No. 08/404,113 filed Mar. 14, 1995) U.S. Ser. No. 923,780 and application Ser. No. 08/260,675, filed May 2, 1995 U.S. Ser. No. 922,813 application Ser. No. 08/260,675, filed Jun. 16, 1994 the disclosures of which are incorporated hereinabove by reference. As described herein, 60A protein (comprising, e.g., Seq. ID NO. 2) may be isolated from natural sources or constructed biosynthetically utilizing conventional recombinant DNA technology.

Morphogenically active fragments of 60A protein (comprising, e.g., Seq. ID NO. 2) are useful for initiating and maintaining the tissue-specific developmental cascade in a variety of tissues, including bone, cartilage, dentin, neural tissue, liver, periodontal ligament, cementum, lung, heart, kidney and numerous tissues of the gastrointestinal tract. When combined with naive progenitor cells as disclosed herein, morphogenically active 60A proteins (comprising, e.g., Seq. ID NO. 2) can induce the proliferation and differentiation of these progenitor cells. In the presence of appropriate tissue-specific signals to direct the differentiation of these cells, and a morphogenically permissive environment, 60A proteins (comprising, e.g., Seq. ID NO. 2) are capable of reproducing the cascade of cellular and molecular events that occur during embryonic development to yield functional tissue. For example, the protein can induce the de novo formation of cartilage and endochondral bone, including inducing the proliferation and differentiation of progenitor cells into chondrocytes and osteoblasts, inducing appropriate mineralization and bone remodeling, inducing formation of an appropriate bone tissue vascular supply and inducing formation of differentiated bone marrow (see Example 7 below.)

Provided below is a detailed description of the 60A proteins (comprising, e.g., Seq. ID NO. 2) useful in the compositions and methods of this invention, a description of how to make them, and methods and means for their therapeutic administration. Also provided are numerous, nonlimiting examples which (1) illustrate the suitability of these proteins as tissue morphogens and therapeutic agents, and (2) provide assays with which to test the morphogens encompassed by the invention in different tissues.

I. Useful Morphogens

As defined herein a protein is morphogenic if it is capable of inducing the developmental cascade of cellular and molecular events that culminate in the formation of new, organ-specific tissue and comprises at least the conserved C-terminal six cysteine skeleton or its functional equivalent (see supra). Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. Details of how the morphogen family of proteins described herein first were identified, as well as a description of how to make, use and test them for morphogenic activity are disclosed in U.S. Ser. No. 667,274, (abandoned in favor of CIP U.S. application Ser. No. 08/404,113, filed Mar. 14, 1995) filed Mar. 11, 1991 and U.S. Ser. No. 752,764, application Ser. No. 08/404,113, filed Mar. 14, 1995 filed Aug. 30, 1991. As disclosed therein, the morphogens may be purified from naturally-sourced material or recombinantly produced from procaryotic or eucaryotic host cells, preferably as described therein, using the genetic sequences disclosed therein. Alternatively, novel morphogenic sequences may be identified following the procedures disclosed therein.

A candidate morphogen or morphogen composition can be evaluated for in vivo morphogenic utility generally according to the procedures set forth in U.S. application Ser. No. 08/404,113, filed Mar. 14, 1995. The proteins and compositions may be injected or surgically implanted in a mammal, following any of a number of procedures well known in the art. For example, surgical implant bioassays may be performed essentially following the procedure of Sampath et al. (1983) *PNAS* 80:6591–6595.

Histological sectioning and staining is preferred to determine the extent of morphogenesis in vivo, particularly in tissue repair procedures. Excised implants are fixed in Bouins Solution, embedded in paraffin, and cut into 6–8 μm sections. Staining with toluidine blue or hemotoxylin/eosin demonstrates clearly the ultimate development of the new tissue. Twelve day implants are usually sufficient to determine whether the implants contain newly induced tissue.

Successful implants exhibit a controlled progression through the stages of induced tissue development allowing one to identify and follow the tissue-specific events that occur. For example, in endochondral bone formation the stages include:

(1) leukocytes on day one;

(2) mesenchymal cell migration and proliferation on days two and three;

(3) chondrocyte appearance on days five and six;

(4) cartilage matrix formation on day seven;

(5) cartilage calcification on day eight;

(6) vascular invasion, appearance of osteoblasts, and formation of new bone on days nine and ten;

(7) appearance of osteoblastic and bone remodeling and dissolution of the implanted matrix on days twelve to eighteen; and (8) hematopoietic bone marrow differentiation in the ossicle on day twenty-one.

In addition to histological evaluation, biological markers may be used as a marker for tissue morphogenesis. Useful markers include tissue-specific enzymes whose activity may be assayed (e.g., spectrophotometrically) after homogenization of the implant. These assays may be useful for quantitation and for obtaining an estimate of tissue formation quickly after the implants are removed from the animal. For example, alkaline phosphatase activity may be used as a marker for osteogenesis.

Incorporation of systemically provided morphogens may be followed using tagged morphogens (e.g., radioactively labelled) and determining their localization in new tissue, and/or by monitoring their disappearance from the circulatory system using a standard pulse-chase labeling protocol. The morphogen also may be provided with a tissue-specific molecular tag, whose uptake may be monitored and correlated with the concentration of morphogen provided. As an example, ovary removal in female rats results in reduced bone alkaline phosphatase activity, rendering the rats predisposed to osteoporosis. If the female rats now are provided with a morphogen, e.g., OP-1, a reduction in the systemic concentration of calcium ($CA^{2+}$) is seen, which correlates with the presence of the provided morphogen and can be shown to correspond to increased alkaline phosphatase activity.

Particularly useful proteins identified to date include OP1 (comprising e.g., Seq. ID NO. 3), OP2 (comprising, e.g., Seq. ID NO. 5), CBMP2A (comprising, e.g., Seq. ID NO. 7) and CBMP2B (comprising, e.g., Seq. ID NO. 8) the morphogenically active domains of proteins referred to in the art as BMP2A and BMP2B, or BMP2 and BMP4, respectively), BMP3 (comprising, e.g., Seq. ID NO. 3), BMP5 (comprised, e.g., Seq. ID NO. 14), BMP6 (comprising, e.g., Seq. ID NO. 15), GDF-1, (comprising, e.g., Seq. ID NO. 12) Vgl, Vgr-1, (comprising, e.g., Seq. ID NO. 12) and (comprising, e.g., Seq. ID NO. 11) DPP, including their allelic and species variants, as well as other mutant variants. Detailed descriptions of the proteins also may be found in, for example, U.S. Ser. No. 922,813 application Ser. No. 08/260,674, filed Jun. 16, 1994. Morphogenically active biosynthetic constructs such as those disclosed in U.S. Pat. No. 5,011,691, the disclosure of which is incorporated herein by reference (e.g., COP-1, COP-3, COP-4, COP-5, COP-7, and COP-16) also are envisioned to be useful.

Recently, the gene encoding a novel member of the TGF-β superfamily of structurally related proteins was identified in the Drosophila genome and named "60A". The cDNA sequence and encoded amino acid sequence ("60A protein") are described in Wharton et al. (1991) *Proc. Natl. Acad. Sci. USA,* 88:9214–9218, and in Seq. ID No. 1.

The Drosphila 60A gene (comprising, e.g., Seq. ID NO. 1) encodes a protein ("60A") first expressed as an immature translation product that is 455 amino acids in length. This precursor form, referred to herein as the "prepro" form, (Seq. ID. No. 1, residues 1–455) includes an N-terminal signal peptide sequence, typically less than about 20 residues, followed by a "pro" domain that is cleaved to yield the mature sequence. The "pro" form of the protein includes the pro domain and the mature domain, and forms a soluble species that appears to be the primary form secreted from cultured mammalian cells. The signal peptide is cleaved rapidly upon translation, at a cleavage site that can be predicted in a given sequence using the method of Von Heijne ((1986) *Nucleic Acids Research* 14:4683–4691).

By amino acid sequence homology with other, known morphogens, the pro domain likely is cleaved at residues 322–325 of Seq. ID NO. 1, which represent the canonical Arg-Xaa-Xaa-Arg (Seq. ID NO. 16) cleavage site, to yield a mature sequence 130 amino acids in length (Seq. ID No. 1, residues 326–455). Another, longer form of the mature sequence is defined by residues 281–455. All morphogens comprise at least a conserved six cysteine skeleton in the amino acid sequence C-terminal domain. The conserved six cysteine skeleton is defined in 60A protein (comprising, e.g., Seq. ID NO. 2) by residues 359–455; the conserved seven cysteine skeleton is defined by residues 354–455. The morphogenically active protein comprises a mature, processed sequence, including fragments thereof, appropriately dimerized and disulfide bonded.

The mature sequence of 60A protein (comprising, e.g., Seq. ID NO. 2) shares significant amino acid sequence homology with the morphogens identified to date. Specifically, the seven cysteine skeleton shows approximately 70% amino acid identity with the corresponding hOP1 sequence. The 60A protein (comprising, e.g., Seq. ID NO. 2) seven cysteine skeleton also shares approximately 73% amino acid identity with the corresponding sequences of Vg-1 , (comprising, e.g., Seq. ID NO. 10) Vgr-1 , (comprising, e.g., Seq. ID NO. 11) BMP5 (comprising, e.g., Seq. ID NO. 14) and BMP6 (comprising, e.g., Seq. ID NO. 15), and about 53% identity with the seven cysteine skeleton of CBMP2A (comprising, e.g., Seq. ID NO. 7) (BMP2) (comprising, e.g., Seq. ID NO. 8) and CBMP2B (BMP4). The 60A protein seven cysteine skeleton also shares about 59% identity with the corresponding sequence of another morphogen identified in Drosophila, DPP (comprising, e.g., Seq. ID NO. 9). Without being limited to a particular theory, based on amino acid homology, 60A protein (comprising, e.g., Seq. ID NO. 2) likely may be the Drosophila homolog or species variant of OP-1 (comprising, e.g., Seq. ID NO. 3).

Table I, set forth below, compares the C-terminal amino acid sequences defining the seven cysteine skeleton of 60A protein (comprising, e.g., Seq. ID NO. 2), native human OP-1 (hOP-1 Seq. ID No. 3), and DPP (from Drosophila), (Seq. ID. No. 9). In the table, three dots indicates that the amino acid in that position is the same as the amino acid in the corresponding position in 60A protein (comprising, e.g., Seq. ID NO. 2). In Table II the sequences of the morphogens OP2, (Seq. ID NO. 5) CBMP2A, (Seq. ID NO. 7) CBMP2B, (Seq. ID NO. 8) BMP3, (Seq. ID NO. 13) BMP5, (Seq. ID NO. 14) BMP6, Vgl, Vgr-1, (Seq. ID NO. 10) GDF-1, (Seq. ID NO. 3) DPP (Seq. ID NO. 9) and 60-A (Seq. ID NO. 2) all are compared to OP-1. (comprising, e.g., Seq. ID NO. 3) In both tables the sequences are aligned essentially following the method of Needleman et al. (1970) *J. Mol. Biol.*, 48:443–453, calculated using the Align Program (DNAstar, Inc.) In the table, three dots indicates that the amino acid in that position is the same as the amino acid in hOP-1 (comprising, e.g., ID NO. 3). Three dashes indicate that no amino acid is present in that position, and are included for purposes of illustrating homologies. For example, amino acid residue 60 of CBMP-2A (comprising, e.g., Seq. ID NO. 7) and CBMP-2B (comprising, e.g., Seq. ID NO. 8) is "missing". Of course, both these amino acid sequences in this region comprise Asn-Ser (residues 58, 59), with CBMP-2A (comprising, e.g., Seq. ID NO. 7) then comprising Lys and Ile, whereas CBMP-2B (comprising, e.g., Seq. ID NO. 8) comprises Ser and Ile.

TABLE I

| | | | | | | | | | |
|---|---|---|---|---|---|---|---|---|---|
| 60A  SEQ. ID. NO. 2 | Cys | Gln | Met | Glu | Thr | Leu | Tyr | Ile | |
| hOP-1 SEQ. ID. NO. 3 | ... | Lys | Lys | His | Glu | ... | ... | Val | |
| DPP   SEQ. ID. NO. 9 | ... | Arg | Arg | ... | Ser | ... | ... | ... | |
| | 1 | | | | 5 | | | | |
| 60A | Asp | Phe | Lys | Asp | Leu | Gly | Trp | His | Asp |
| hOP-1 | Ser | ... | Arg | ... | ... | ... | ... | Gln | ... |
| DPP | Asp | ... | Ser | ... | Val | ... | ... | Asp | ... |
| | | 10 | | | | | 15 | | |
| 60A | Trp | Ile | Ile | Ala | Pro | Glu | Gly | Tyr | Gly |
| hOP-1 | ... | ... | ... | ... | ... | ... | ... | ... | Ala |
| DPP | ... | ... | Val | ... | ... | Leu | ... | ... | Asp |
| | | | 20 | | | | | 25 | |
| 60A | Ala | Phe | Tyr | Cys | Ser | Gly | Glu | Cys | Asn |
| hOP-1 | ... | Tyr | ... | ... | Glu | ... | ... | ... | Ala |
| DPP | ... | ... | ... | ... | His | ... | Lys | ... | Pro |
| | | | | 30 | | | | | 35 |
| 60A | Phe | Pro | Leu | Asn | Ala | His | Het | Asn | Ala |
| hOP-1 | ... | ... | ... | ... | Ser | Tyr | ... | ... | ... |
| DPP | ... | ... | ... | Ala | Asp | His | Phe | ... | Ser |
| | | | | | 40 | | | | |
| 60A | Thr | Asn | His | Ala | Ile | Val | Glu | Thr | Leu |
| hOP-1 | ... | ... | ... | ... | ... | ... | ... | ... | ... |
| DPP | ... | ... | ... | ... | Val | ... | ... | ... | ... |
| | 45 | | | | | 50 | | | |
| 60A | Val | His | Leu | Leu | Glu | Pro | Lys | Lys | Val |
| hOP-1 | ... | ... | Phe | Ile | Asn | ... | Glu | Thr | ... |
| DPP | ... | Asn | Asn | Asn | ... | ... | Gly | Lys | ... |
| | | 55 | | | | | 60 | | |
| 60A | Pro | Lys | Pro | Cys | Cys | Ala | Pro | Thr | Arg |
| hOP-1 | ... | ... | ... | ... | ... | ... | ... | ... | Gln |
| DPP | ... | ... | Ala | ... | ... | Val | ... | ... | ... |
| | | | 65 | | | | | 70 | |
| 60A | Leu | Gly | Ala | Leu | Pro | Val | Leu | Tyr | His |
| hOP-1 | ... | Asn | ... | Ile | Ser | ... | ... | ... | Phe |
| DPP | ... | Asp | Ser | Val | Ala | Met | ... | ... | Leu |
| | | | | 75 | | | | | 80 |
| 60A | Leu | Asn | Asp | Glu | Asn | Val | Asn | Leu | Lys |
| hOP-1 | Asp | Asp | Ser | Ser | ... | ... | Ile | ... | ... |
| DPP | Asn | ... | Gln | ... | Thr | ... | Val | ... | ... |
| | | | | | 85 | | | | |
| 60A | Lys | Tyr | Arg | Asn | Met | Ile | Val | Lys | |
| hOP-1 | ... | ... | ... | ... | ... | Val | ... | Arg | |
| DPP | Asn | ... | Gln | Glu | ... | Thr | ... | Val | |
| | 90 | | | | | 95 | | | |
| 60A | Ser | Cys | Gly | Cys | His | | | | |
| hOP-1 | Ala | ... | ... | ... | ... | | | | |
| DPP | Gly | ... | ... | ... | Arg | | | | |
| | | | 100 | | | | | | |

TABLE II

| | | Cys | Lys | Lys | His | Glu | Leu | Tyr | Val |
|---|---|---|---|---|---|---|---|---|---|
| hOP-1 | SEQ. ID. NO. 3 | Cys | Lys | Lys | His | Glu | Leu | Tyr | Val |
| mOP-1 | SEQ. ID. NO. 4 | ... | ... | ... | ... | ... | ... | ... | ... |
| hOP-2 | SEQ. ID. NO. 5 | ... | Arg | Arg | ... | ... | ... | ... | ... |
| mOP-2 | SEQ. ID. NO. 6 | ... | Arg | Arg | ... | ... | ... | ... | ... |
| DPP | SEQ. ID. NO. 9 | ... | Arg | Arg | ... | Ser | ... | ... | ... |
| Vgl | SEQ. ID. NO. 10 | ... | ... | Lys | Arg | His | ... | ... | ... |
| Vgr-1 | SEQ. ID. NO. 11 | ... | ... | ... | ... | Gly | ... | ... | ... |
| CBMP-2A | SEQ. ID. NO. 7 | ... | ... | Arg | ... | Pro | ... | ... | ... |
| CBMP-2B | SEQ. ID. NO. 8 | ... | Arg | Arg | ... | Ser | ... | ... | ... |
| BMP3 | SEQ. ID. NO. 13 | ... | Ala | Arg | Arg | Tyr | ... | Lys | ... |
| GDF-1 | SEQ. ID. NO. 12 | ... | Arg | Ala | Arg | Arg | ... | ... | ... |
| 60A | SEQ. ID. NO. 2 | ... | Gln | Met | Glu | Thr | ... | ... | ... |
| BMP5 | SEQ. ID. NO. 14 | ... | ... | ... | ... | ... | ... | ... | ... |
| BMP6 | SEQ. ID. NO. 15 | ... | Arg | ... | ... | ... | ... | ... | ... |

| | 1 | | | | 5 | | | | |
|---|---|---|---|---|---|---|---|---|---|
| hOP-1 | Ser | Phe | Arg | Asp | Leu | Gly | Trp | Gln | Asp |
| mOP-1 | ... | ... | ... | ... | ... | ... | ... | ... | ... |
| hOP-2 | ... | ... | Gln | ... | ... | ... | ... | Leu | ... |
| mOP-2 | Ser | ... | ... | ... | ... | ... | ... | Leu | ... |
| DPP | Asp | ... | Ser | ... | Val | ... | ... | Asp | ... |
| Vgl | Glu | ... | Lys | ... | Val | ... | ... | ... | Asn |
| Vgr-1 | ... | ... | Gln | ... | Val | ... | ... | ... | ... |
| CBMP-2A | Asp | ... | Ser | ... | Val | ... | ... | Asn | ... |
| CBMP-2B | Asp | ... | Ser | ... | Val | ... | ... | Asn | ... |
| BMP3 | Asp | ... | Ala | ... | Ile | ... | ... | Ser | Glu |
| GDF-1 | ... | ... | ... | Glu | Val | ... | ... | His | Arg |
| 60A | Asp | ... | Lys | ... | ... | ... | ... | His | ... |
| BMP5 | ... | ... | ... | ... | ... | ... | ... | ... | ... |
| BMP6 | ... | ... | Gln | ... | ... | ... | ... | ... | ... |

| | 10 | | | | | 15 | | | |
|---|---|---|---|---|---|---|---|---|---|
| hOP-1 | Trp | Ile | Ile | Ala | Pro | Glu | Gly | Tyr | Ala |
| mOP-1 | ... | ... | ... | ... | ... | ... | ... | ... | ... |
| hOP-2 | ... | Val | ... | ... | ... | Gln | ... | ... | Ser |
| mOP-2 | ... | Val | ... | ... | ... | Gln | ... | ... | Ser |
| DPP | ... | ... | Val | ... | ... | Leu | ... | ... | Asp |
| Vgl | ... | Val | ... | ... | ... | Gln | ... | ... | Met |
| Vgr-1 | ... | ... | ... | ... | ... | Lys | ... | ... | ... |
| CBMP-2A | ... | ... | Val | ... | ... | Pro | ... | ... | His |
| CBMP-2B | ... | ... | Val | ... | ... | Pro | ... | ... | Gln |
| BMP3 | ... | ... | ... | Ser | ... | Lys | Ser | Phe | Asp |
| GDF-1 | ... | Val | ... | ... | ... | Arg | ... | Phe | Leu |
| 60A | ... | ... | ... | ... | ... | ... | ... | ... | Gly |
| BMP5 | ... | ... | ... | ... | ... | ... | ... | ... | ... |
| BMP6 | ... | ... | ... | ... | ... | Lys | ... | ... | ... |

| | | | 20 | | | | 25 | | |
|---|---|---|---|---|---|---|---|---|---|
| hOP-1 | Ala | Tyr | Tyr | Cys | Glu | Gly | Glu | Cys | Ala |
| mOP-1 | ... | ... | ... | ... | ... | ... | ... | ... | ... |
| hOP-2 | ... | ... | ... | ... | ... | ... | ... | ... | Ser |
| mOP-2 | ... | ... | ... | ... | ... | ... | ... | ... | ... |
| DPP | ... | ... | ... | ... | His | ... | Lys | ... | Pro |
| Vgl | ... | Asn | ... | ... | Tyr | ... | ... | ... | Pro |
| Vgr-1 | ... | Asn | ... | ... | Asp | ... | ... | ... | Ser |
| CBMP-2A | ... | Phe | ... | ... | His | ... | Glu | ... | Pro |
| CBMP-2B | ... | Phe | ... | ... | His | ... | Asp | ... | Pro |
| BMP3 | ... | ... | ... | ... | Ser | ... | Ala | ... | Gln |
| GDF-1 | ... | Asn | ... | ... | Gln | ... | Gln | ... | ... |
| 60A | ... | Phe | ... | ... | Ser | ... | ... | ... | Asn |
| BMP5 | ... | Phe | ... | ... | Asp | ... | ... | ... | Ser |
| BMP6 | ... | Asn | ... | ... | Asp | ... | ... | ... | Ser |

| | | | | 30 | | | | 35 | |
|---|---|---|---|---|---|---|---|---|---|
| hOP-1 | Phe | Pro | Leu | Asn | Ser | Tyr | Met | Asn | Ala |
| mOP-1 | ... | ... | ... | ... | ... | ... | ... | ... | ... |
| hOP-2 | ... | ... | ... | Asp | ... | Cys | ... | ... | ... |
| mOP-2 | ... | ... | ... | Asp | ... | Cys | ... | ... | ... |
| DPP | ... | ... | ... | Ala | Asp | His | Phe | ... | Ser |
| Vgl | Tyr | ... | ... | Thr | Glu | Ile | Leu | ... | Gly |
| Vgr-1 | ... | ... | ... | ... | Ala | His | ... | ... | ... |
| CBMP-2A | ... | ... | ... | Ala | Asp | His | Leu | ... | Ser |
| CBMP-2B | ... | ... | ... | Ala | Asp | His | Leu | ... | Ser |
| GDF-1 | Leu | ... | Val | Ala | Leu | Ser | Gly | Ser** | ... |
| BMP3 | ... | ... | Met | Pro | Lys | Ser | Leu | Lys | Pro |
| 60A | ... | ... | ... | ... | Ala | His | ... | ... | ... |
| BMP5 | ... | ... | ... | ... | Ala | His | Met | ... | ... |
| BMP6 | ... | ... | ... | ... | Ala | His | Met | ... | ... |

| | | | | | 40 | | | | |
|---|---|---|---|---|---|---|---|---|---|
| hOP-1 | Thr | Asn | His | Ala | Ile | Val | Gln | Thr | Leu |
| mOP-1 | ... | ... | ... | ... | ... | ... | ... | ... | ... |
| hOP-2 | ... | ... | ... | ... | ... | Leu | ... | Ser | ... |
| mOP-2 | ... | ... | ... | ... | ... | Leu | ... | Ser | ... |

TABLE II-continued

| | | | | | | | | |
|---|---|---|---|---|---|---|---|---|
| DPP | ... | ... | ... | ... | Val | ... | ... | ... |
| Vgl | Ser | ... | ... | ... | ... | Leu | ... | ... | ... |
| Vgr-1 | ... | ... | ... | ... | ... | ... | ... | ... |
| CBMP-2A | ... | ... | ... | ... | ... | ... | ... | ... |
| CBMP-2B | ... | ... | ... | ... | ... | ... | ... | ... |
| BMP3 | Ser | ... | ... | ... | Thr | Ile | ... | Ser | Ile |
| GDF-1 | Leu | ... | ... | ... | Val | Leu | Arg | Ala | ... |
| 60A | ... | ... | ... | ... | ... | ... | ... | ... |
| BMP5 | ... | ... | ... | ... | ... | ... | ... | ... |
| BMP6 | ... | ... | ... | ... | ... | ... | ... | ... |
| | 45 | | | | 50 | | | |
| hOP-1 | Val | His | Phe | Ile | Asn | Pro | Glu | Thr | Val |
| mOP-1 | ... | ... | ... | ... | ... | ... | Asp | ... | ... |
| hOP-2 | ... | His | Leu | Met | Lys | ... | Asn | Ala | ... |
| mOP-2 | ... | His | Leu | Met | Lys | ... | Asp | Val | ... |
| DPP | ... | Asn | Asn | Asn | ... | ... | Gly | Lys | ... |
| Vgl | ... | ... | Ser | ... | Glu | ... | ... | Asp | Ile |
| Vgr-1 | ... | ... | Val | Met | ... | ... | ... | Tyr | ... |
| CBMP-2A | ... | Asn | Ser | Val | ... | Ser | --- | Lys | Ile |
| CBMP-2B | ... | Asn | Ser | Val | ... | Ser | --- | Ser | Ile |
| BMP3 | ... | Arg | Ala** | Gly | Val | Val | Pro | Gly | Ile |
| GDF-1 | Met | ... | Ala | Ala | Ala | ... | Gly | Ala | Ala |
| 60A | ... | ... | Leu | Leu | Glu | ... | Lys | Lys | ... |
| BMP5 | ... | ... | Leu | Met | Phe | ... | Asp | His | ... |
| BMP6 | ... | ... | Leu | Met | ... | ... | ... | Tyr | ... |
| | | 55 | | | | 60 | | |
| hOP-1 | Pro | Lys | Pro | Cys | Cys | Ala | Pro | Thr | Gln |
| mOP-1 | ... | ... | ... | ... | ... | ... | ... | ... | ... |
| hOP-2 | ... | ... | Ala | ... | ... | ... | ... | ... | Lys |
| mOP-2 | ... | ... | Ala | ... | ... | ... | ... | ... | Lys |
| DPP | ... | ... | Ala | ... | ... | Val | ... | ... | ... |
| Vgl | ... | Leu | ... | ... | ... | Val | ... | ... | Lys |
| Vgr-1 | ... | ... | ... | ... | ... | ... | ... | ... | Lys |
| CBMP-2A | ... | ... | Ala | ... | ... | Val | ... | ... | Glu |
| CBMP-2B | ... | ... | Ala | ... | ... | Val | ... | ... | Glu |
| BMP3 | ... | Glu | ... | ... | ... | Val | ... | Glu | Lys |
| GDF-1 | Asp | Leu | ... | ... | ... | Val | ... | Ala | Arg |
| 60A | ... | ... | ... | ... | ... | ... | ... | ... | Arg |
| BMP5 | ... | ... | ... | ... | ... | ... | ... | ... | Lys |
| BMP6 | ... | ... | ... | ... | ... | ... | ... | ... | Lys |
| | | | 65 | | | | 70 | |
| hOP-1 | Leu | Asn | Ala | Ile | Ser | Val | Leu | Tyr | Phe |
| mOP-1 | ... | ... | ... | ... | ... | ... | ... | ... | ... |
| hOP-2 | ... | Ser | ... | Thr | ... | ... | ... | ... | Tyr |
| mOP-2 | ... | Ser | ... | Thr | ... | ... | ... | ... | Tyr |
| Vgl | Met | Ser | Pro | ... | ... | Met | ... | Phe | Tyr |
| Vgr-1 | Val | ... | ... | ... | ... | ... | ... | ... | ... |
| DPP | ... | Asp | Ser | Val | Ala | Met | ... | ... | Leu |
| CBMP-2A | ... | Ser | ... | ... | ... | Met | ... | ... | Leu |
| CBMP-2B | ... | Ser | ... | ... | ... | Met | ... | ... | Leu |
| BMP3 | Met | Ser | Ser | Leu | ... | Ile | ... | Phe | Tyr |
| GDF-1 | ... | Ser | Pro | ... | ... | ... | ... | Phe | ... |
| 60A | ... | Gly | ... | Leu | Pro | ... | ... | ... | His |
| BMP5 | ... | ... | ... | ... | ... | ... | ... | ... | ... |
| BMP6 | ... | ... | ... | ... | ... | ... | ... | ... | ... |
| | | | | 75 | | | | 80 |
| hOP-1 | Asp | Asp | Ser | Ser | Asn | Val | Ile | Leu | Lys |
| mOP-1 | ... | ... | ... | ... | ... | ... | ... | ... | ... |
| hOP-2 | ... | Ser | ... | Asn | ... | ... | ... | ... | Arg |
| mOP-2 | ... | Ser | ... | Asn | ... | ... | ... | ... | Arg |
| DPP | Asn | ... | Gln | ... | Thr | ... | Val | ... | ... |
| Vgl | ... | Asn | Asn | Asp | ... | ... | Val | ... | Arg |
| Vgr-1 | ... | ... | Asn | ... | ... | ... | ... | ... | ... |
| CBMP-2A | ... | Glu | Asn | Glu | Lys | ... | Val | ... | ... |
| CBMP-2B | ... | Glu | Tyr | Asp | Lys | ... | Val | ... | ... |
| BMP3 | ... | Glu | Asn | Lys | ... | ... | Val | ... | ... |
| GDF-1 | ... | Asn | ... | Asp | ... | ... | Val | ... | Arg |
| 60A | Leu | Asn | Asp | Glu | ... | ... | Asn | ... | ... |
| BMP5 | ... | ... | ... | ... | ... | ... | ... | ... | ... |
| BMP6 | ... | ... | Asn | ... | ... | ... | ... | ... | ... |
| | | | | | 85 | | | |
| hOP-1 | Lys | Tyr | Arg | Asn | Met | Val | Val | Arg | |
| mOP-1 | ... | ... | ... | ... | ... | ... | ... | ... | |
| hOP-2 | ... | His | ... | ... | ... | ... | ... | Lys | |
| mOP-2 | ... | His | ... | ... | ... | ... | ... | Lys | |
| DPP | Asn | ... | Gln | Glu | ... | Thr | ... | Val | |
| Vgl | His | ... | Glu | ... | ... | Ala | ... | Asp | |
| Vgr-1 | ... | ... | ... | ... | ... | ... | ... | ... | |
| CBMP-2A | Asn | ... | Gln | Asp | ... | ... | ... | Glu | |

TABLE II-continued

| | | | | | | | | |
|---|---|---|---|---|---|---|---|---|
| CBMP-2B | Asn | ... | Gln | Glu | ... | ... | ... | Glu |
| BMP3 | Val | ... | Pro | ... | ... | Thr | ... | Glu |
| GDF-1 | Gln | ... | Glu | Asp | ... | ... | ... | Asp |
| 60A | ... | ... | ... | ... | ... | Ile | ... | Lys |
| BMP5 | ... | ... | ... | ... | ... | ... | ... | ... |
| BMP6 | ... | ... | ... | Trp | ... | ... | ... | ... |
| | 90 | | | | | 95 | | |
| hOP-1 | Ala | Cys | Gly | Cys | His | | | |
| mOP-1 | ... | ... | ... | ... | ... | | | |
| hOP-2 | ... | ... | ... | ... | ... | | | |
| mOP-2 | ... | ... | ... | ... | ... | | | |
| DPP | Gly | ... | ... | ... | Arg | | | |
| Vgl | Glu | ... | ... | ... | Arg | | | |
| Vgr-1 | ... | ... | ... | ... | ... | | | |
| CBMP-2A | Gly | ... | ... | ... | Arg | | | |
| CBMP-2B | Gly | ... | ... | ... | Arg | | | |
| BMP3 | Ser | ... | Ala | ... | Arg | | | |
| GDF-1 | Glu | ... | ... | ... | Arg | | | |
| 60A | Ser | ... | ... | ... | ... | | | |
| BMP5 | Ser | ... | ... | ... | ... | | | |
| BMP6 | ... | ... | ... | ... | ... | | | |
| | | | 100 | | | | | |

**Between residues 56 and 57 of BMP3 (comprising, e.q., SEQ ID NO:13) is a Val residue; between residues 43 and 44 of GDF-1 (comprising, e.q., SEQ ID NO:12) lies the amino acid sequence Gly-Gly-Pro-Pro.

As is apparent from the foregoing amino acid sequence comparisons, significant amino acid changes can be made within the sequences while retaining the morphogenic activity. For example, while the GDF-1 (comprising, e.g., Seq. ID NO. 12) protein sequence depicted in Table II shares only about 50% amino acid identity with the hOP-1 (comprising, e.g., Seq. ID NO. 3) sequence described therein, the GDF-1 (comprising, e.g., Seq. ID NO. 12) sequence shares greater than 70% amino acid sequence homology (or "similarity") with the hOP-1 sequence (comprising, e.g., Seq. ID NO. 3), where "homology" or "similarity" includes allowed conservative amino acid changes within the sequence as defined by Dayoff, et al., *Atlas of Protein Sequence and Structure* vol.5, supp.3, pp.345–362, (M. O. Dayoff, ed., Nat'l BioMed. Res. Fd'n, Washington D.C. 1979.)

II. Formulations and Methods for Administering 60A Protein as Therapeutic Agents II.A 60A Protein Considerations The morphogens described herein may be provided to an individual by any suitable means, preferably directly or systemically, e.g., parenterally or orally. Where the morphogen is to be provided directly (e.g., locally, as by injection, to a desired tissue site), or parenterally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the morphogen preferably comprises part of an aqueous solution. The solution is physiologically acceptable so that in addition to delivery of the desired morphogen to the patient, the solution does not otherwise adversely affect the patient's electrolyte and volume balance. The aqueous medium for the morphogen thus may comprise normal physiologic saline (0.85% NaCl, 0.15M), pH 7–7.4. The aqueous solution containing the morphogen can be made, for example, by dissolving the protein in 50% ethanol, acetonitrile containing 0.1% trifluoroacetic acid (TFA) or 0.1% HCl, or equivalent solvents. One volume of the resultant solution then is added, for example, to ten volumes of phosphate buffered saline (PBS), which further may include 0.1–0.2% human serum albumin (HSA). The resultant solution preferably is vortexed extensively. If desired, a given morphogen may be made more soluble by association with a suitable molecule. For example, the pro form of 60A protein (comprising, e.g., Seq. ID NO. 2) comprises a species that is soluble in physiological solutions. In fact, the endogenous protein is thought to be transported (e.g., secreted and circulated) to particular tissues in this form. This soluble form of the protein may be obtained from the culture medium of morphogen-secreting mammalian cells. Alternatively, a soluble species may be formulated by complexing the mature dimer (or an active fragment thereof) with part or all of a pro domain. Another molecule capable of enhancing solubility and particularly useful for oral administrations, is casein. For example, addition of 0.2% casein increases solubility of the mature active form of OP-1 (comprising, e.g., Seq. ID NO. 3) by 80%. Other components found in milk and/or various serum proteins also may be useful.

Useful solutions for oral or parenteral administration may be prepared by any of the methods well known in the pharmaceutical art, described, for example, in *Remington's Pharmaceutical Sciences*, (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscosity. Biocompatible, preferably bioresorbable polymers, including, for example, hyaluronic acid, collagen, tricalcium phosphate, polybutyrate, polyglycolide, polylactide and lactide/glycolide copolymers, may be useful excipients to control the release of the morphogen in vivo. Other potentially useful parenteral delivery systems for these morphogens include ethylene-vinyl acetate copolymer particles, osmotic pumps, implantable infusion systems, and liposomes. Formulations for inhalation administration may contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or cutric acid for vaginal administration.

Alternatively, the morphogens described herein may be administered orally. Oral administration of proteins as therapeutics generally is not practiced as most proteins readily are degraded by digestive enzymes and acids in the mammalian digestive system before they can be absorbed into the bloodstream. However, the morphogens described herein typically are acid-stable and protease-resistant (see, for example, U.S. Pat. No. 4,968,590.) In addition, at least one morphogen, OP-1, (comprising, e.g., Seq. ID NO. 3) has been identified in bovine mammary gland extract, colostrum and milk, as well as saliva. Moreover, the OP-1 (comprising, e.g., Seq. ID NO. 3) purified from mammary gland extract is morphogenically active. For example, this protein induces endochondral bone formation in mammals when implanted subcutaneously in association with a suitable matrix material, using a standard in vivo bone assay, such as is disclosed in U.S. Pat. No. 4,968,590. In addition, endogenous morphogen also is detected in human serum. These findings indicate that oral and parenteral administration are viable means for administering morphogens to an individual. Moreover, while the mature forms of certain morphogens described herein typically are sparingly soluble, the morphogen form found in milk (and mammary gland extract and colostrum) is readily soluble, probably by association of the mature, morphogenically active form with the pro domain of the intact sequence and/or by association with one or more milk components. Accordingly, the compounds provided herein also may be associated with molecules capable of enhancing their solubility in vitro or in vivo, including, for example, part or all of a morphogen pro domain, and casein, as described above.

The compounds provided herein also may be associated with molecules capable of targeting the morphogen to a desired tissue. For example, tetracycline and diphosphonates (bisphosphonates) are known to bind to bone mineral, particularly at zones of bone remodeling, when they are provided systemically in a mammal. Accordingly, these molecules may be included as useful agents for targeting 60A protein (comprising, e.g., Seq. ID NO. 2) to bone tissue. Alternatively, an antibody or other binding protein that interacts specifically with a surface molecule on the desired target tissue cells also may be used. Such targeting molecules further may be covalently associated to the morphogen with, for example, an acid labile bond such as an Asp-Pro linkage, using standard chemical means well known in the art. Useful targeting molecules may be designed, for example, using the single chain binding site technology disclosed, for example, in U.S. Pat. No. 5,091,513.

As described above, the morphogen family members share significant sequence homology in the C-terminal active domains. By contrast, the sequences diverge significantly in the sequences which define the pro domain. Accordingly, the pro domain may be morphogen-specific. As described above, it also is known that the various morphogens identified to date are differentially expressed in the different tissues. Accordingly, without being limited to any given theory, it is likely that, under natural conditions in the body, selected morphogens typically act on a given tissue. Accordingly, part or all of morphogen pro domains may serve as targeting molecules for the morphogens described herein. For example, the pro domains may interact specifically with one or more molecules at the target tissue to direct the morphogen associated with the pro domain to that tissue. Accordingly, another useful targeting molecule for targeting 60A protein (comprising, e.g., Seq. ID NO. 2) to bone tissue, for example, may include part or all of a morphogen pro domain, particularly part or all of the pro domains of OP-1, (comprising, e.g., Seq. ID NO. 3) BMP2 or BMP4, all of which proteins are found naturally associated with bone tissue (see, for example, U.S. Pat. No. 5,011,691). Alternatively, the pro domain of GDF-1 (comprising, e.g., Seq. ID NO. 12) may be used to target morphogenic 60A protein (comprising, e.g., Seq. ID NO. 2) to nerve tissue, particularly brain tissue where GDF-1 (comprising, e.g., Seq. ID NO. 12) appears to be primarily expressed (see, for example, CRP070 and Lee(1991) *PNAS:*88:4250–4254, incorporated herein by reference). As described above, morphogen species comprising the pro domain may be obtained from the culture medium of morphogen-secreting mammalian cells. Alternatively, a tissue-targeting species may be formulated by complexing the mature dimer (or an active fragment thereof) with part or all of a pro domain.

Finally, the morphogenic 60A proteins (comprising, e.g., Seq. ID NO. 2) provided herein may be administered alone or in combination with other molecules known to have a beneficial effect on tissue morphogenesis, including molecules capable of tissue repair and regeneration and/or inhibiting inflammation. Examples of useful cofactors for stimulating bone tissue growth in osteoporotic individuals, for example, include vitamin $D_3$, calcitonin, prostaglandins, parathyroid hormone, dexamethasone, estrogen and IGF-I or IGF-II. Useful cofactors for nerve tissue repair and regneration may include nerve growth factors.

The compounds provided herein can be formulated into pharmaceutical compositions by admixture with pharmaceutically acceptable nontoxic excipients and carriers. As noted above, such compositions may be prepared for parenteral administration, particularly in the form of liquid solutions or suspensions; for oral administration, particularly in the form of tablets or capsules; or intranasally, particularly in the form of powders, nasal drops, or aerosols.

The compositions can be formulated for parenteral or oral administration to humans or other mammals in therapeutically effective amounts, e.g., amounts which provide appropriate concentrations of a morphogenic 60A protein to target tissue for a time sufficient to induce morphogenesis, including particular steps thereof, as described above.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of tissue loss or defect, the overall health status of the particular patient, the relative biological efficacy of the compound selected, the formulation of the compound excipients, and its route of administration. In general terms, the compounds of this invention may be provided in an aqueous physiological buffer solution containing about 0.1 to 10% w/v compound for parenteral administration. Typical dose ranges are from about 10 ng/kg to about 1 g/kg of body weight per day; a preferred dose range is from about 0.1 $\mu$g/kg to 100 mg/kg of body weight per day. Optimally, the 60A protein (comprising, e.g., Seq. ID NO. 2) dosage given in all cases is between 1–100 $\mu$g of protein per kilogram weight of the patient. Currently preferred dose ranges for local injection of soluble 60A protein (comprising, e.g., Seq. ID NO. 2) to target tissue are 0.1–50 $\mu$g morphogen/injection. No obvious morphogen-induced pathological lesions are induced when mature morphogen (e.g., OP-1, 20 $\mu$g) is administered daily to normal growing rats for 21 consecutive days. Moreover, 10 $\mu$g systemic injections of morphogen (e.g., OP-1

(comprising, e.g., Seq. ID NO. 3)) injected daily for 10 days into normal newborn mice does not produce any gross abnormalities.

II.B Matrix Preparation

A morphogenically active fragment of 60A protein may be implanted surgically, dispersed in a biocompatible, preferably in vivo biodegradable matrix appropriately modified to provide a structure in which the 60A protein (comprising, e.g., Seq. ID NO. 2) may be dispersed and which allows the influx, differentiation and proliferation of migrating progenitor cells. The matrix also may provide signals capable of directing the tissue specificity of the differentiating cells, as well as providing a morphogenically permissive environment, being essentially free of growth inhibiting signals.

The formulated matrix may be shaped as desired in anticipation of surgery or may be shaped by the physician or technician during surgery. Thus, the material may be used in topical, subcutaneous, intraperitoneal, or intramuscular implants to repair tissue or to induce its growth de novo. The matrix preferably is biodegradable in vivo, being slowly absorbed by the body and replaced by new tissue growth, in the shape or very nearly in the shape of the implant.

Details of how to make and how to use the matrices useful in this invention are disclosed below and in co-pending U.S. Ser. No. 667,274 (abandoned in favor of CIP U.S. application Ser. No. 08/404,113, filed Mar. 14, 1995) and 752,764 application Ser. No. 08/404,113, filed Mar. 14, 1995 the disclosures of which are incorporated herein by reference.

II.B(i) Tissue-Derived Matrices

Suitable biocompatible, in vivo biodegradable acellular matrices may be prepared from naturally-occurring tissue. The tissue is treated with suitable agents to substantially extract the cellular, nonstructural components of the tissue. The agents also should be capable of extracting any growth inhibiting components associated with the tissue. The resulting material is a porous, acellular matrix, substantially depleted in nonstructurally-associated components.

The matrix also may be further treated with agents that modify the matrix, increasing the number of pores and micropits on its surfaces. Those skilled in the art will know how to determine which agents are best suited to the extraction of nonstructural components for different tissues. For example, soft tissues such as liver and lung may be thin-sectioned and exposed to a nonpolar solvent such as, for example, 100% ethanol, to destroy the cellular structure of the tissue and extract nonstructural components. The material then is dried and pulverized to yield nonadherent porous particles. Structural tissues such as cartilage and dentin where collagen is the primary component may be demineralized and extracted with guanidine, essentially following the method of Sampath et al. (1983) *PNAS* 80:6591–6595. For example, pulverized and demineralized dentin is extracted with five volumes of 4M guanidine-HCl, 50 mM Tris-HCl, pH 7.0 for 16 hours at 4° C. The suspension then is filtered. The insoluble material that remains is collected and used to fabricate the matrix. The material is mostly collagenous in matter. It is devoid of morphogenic activity. The matrix particles may further be treated with a collagen fibril-modifying agent that extracts potentially unwanted components from the matrix, and alters the surface structure of the matrix material. Useful agents include acids, organic solvents or heated aqueous media. A detailed description of these matrix treatments are disclosed, for example, in U.S. Pat. No. 4,975,526 and PCT publication US90/00912, published Sep. 7, 1990 (WO90/10018).

The currently most preferred agent is a heated aqueous fibril-modifying medium such as water, to increase the matrix particle surface area and porosity. The currently most preferred aqueous medium is an acidic aqueous medium having a pH of less than about 4.5, e.g., within the range of about pH 2–pH 4 which may help to "swell" the collagen before heating. 0.1% acetic acid, which has a pH of about 3, currently is most preferred. 0.1 M acetic acid also may be used.

Various amounts of delipidated, demineralized guanidine-extracted bone collagen are heated in the aqueous medium (1 g matrix/30 ml aqueous medium) under constant stirring in a water jacketed glass flask, and maintained at a given temperature for a predetermined period of time. Preferred treatment times are about one hour, although exposure times of between about 0.5 to two hours appear acceptable. The temperature employed is held constant at a temperature within the range of about 37° C. to 65° C. The currently preferred heat treatment temperature is within the range of about 45° C. to 60° C.

After the heat treatment, the matrix is filtered, washed, lyophilized and used for implant. Where an acidic aqueous medium is used, the matrix also is preferably neutralized prior to washing and lyophilization. A currently preferred neutralization buffer is a 200 mM sodium phosphate buffer, pH 7.0. To neutralize the matrix, the matrix preferably first is allowed to cool following thermal treatment, the acidic aqueous medium (e.g., 0.1% acetic acid) then is removed and replaced with the neutralization buffer and the matrix agitated for about 30 minutes. The neutralization buffer then may be removed and the matrix washed and lyophilized.

Other useful fibril-modifying treatments include acid treatments (e.g., trifluoroacetic acid and hydrogen fluoride) and solvent treatments such as dichloromethane, acetonitrile, isopropanol and chloroform, as well as particular acid/solvent combinations.

After contact with the fibril-modifying agent, the treated matrix may be washed to remove any extracted components, following a form of the procedure set forth below:

1. Suspend matrix preparation in TBS (Tris-buffered saline) 1 g/200 ml and stir at 4° C. for 2 hrs; or in 6 M urea, 50 mM Tris-HCl, 500 mM NaCl, pH 7.0 (UTBS) or water and stir at room temperature (RT) for 30 minutes (sufficient time to neutralize the pH);

2. Centrifuge and repeat wash step; and

3. Centrifuge; discard supernatant; water wash residue; and then lyophilize.

II.B(ii) Synthetic Tissue-Specific Matrices

In addition to the naturally-derived tissue-specific matrices described above, useful tissue-specific matrices may be formulated synthetically if appropriately modified. These porous biocompatible, in vivo biodegradable synthetic matrices are disclosed in PCT publication US91/03603, published Dec. 12, 1991 (WO91/18558), the disclosure of which is hereby incorporated by reference. Briefly, the matrix comprises a porous crosslinked structural polymer of biocompatible, biodegradable collagen and appropriate, tissue-specific glycosaminoglycans as tissue-specific cell attachment factors. Collagen derived from a number of sources may be suitable for use in these synthetic matrices, including insoluble collagen, acid- soluble collagen, collagen soluble in neutral or basic aqueous solutions, as well as those collagens which are commercially available.

Glycosaminoglycans (GAGs) or mucopolysaccharides are hexosamine-containing polysaccharides of animal origin that have a tissue specific distribution, and therefore may be used to help determine the tissue specificity of the morphogen-stimulated differentiating cells. Reaction with the GAGs also provides collagen with another valuable property, i.e., inability to provoke an immune reaction (foreign body reaction) from an animal host.

Chemically, GAGs are made up of residues of hexosamines glycosidically bound and alternating in a more-or-less regular manner with either hexouronic acid or hexose moieties (see, e.g., Dodgson et al. in *Carbohydrate Metabolism and its Disorders* (Dickens et al., eds.) Vol. 1, Academic Press (1968)). Useful GAGs include hyaluronic acid, heparin, heparin sulfate, chondroitin 6-sulfate, chondroitin 4-sulfate, dermatan sulfate, and keratin sulfate. Other GAGs are suitable for forming the matrix described herein, and those skilled in the art will either know or be able to ascertain other suitable GAGs using no more than routine experimentation. For a more detailed description of mucopolysaccharides, see Aspinall, *Polysaccharides*, Pergamon Press, Oxford (1970). For example, as disclosed in U.S. application Ser. No. 529,852, chondroitin-6-sulfate can be used where endochondral bone formation is desired. Heparin sulfate, on the other hand, may be used to formulate synthetic matrices for use in lung tissue repair.

Collagen can be reacted with a GAG in aqueous acidic solutions, preferably in diluted acetic acid solutions. By adding the GAG dropwise into the aqueous collagen dispersion, coprecipitates of tangled collagen fibrils coated with GAG results. This tangled mass of fibers then can be homogenized to form a homogeneous dispersion of fine fibers and then filtered and dried.

Insolubility of the collagen-GAG products can be raised to the desired degree by covalently cross-linking these materials, which also serves to raise the resistance to resorption of these materials. In general, any covalent cross-linking method suitable for cross-linking collagen also is suitable for cross-linking these composite materials, although crosslinking by a dehydrothermal process is preferred.

When dry, the crosslinked particles are essentially spherical, with diameters of about 500 $\mu$m. Scanning electron miscroscopy shows pores of about 20 $\mu$m on the surface and 40 $\mu$m on the interior. The interior is made up of both fibrous and sheet-like structures, providing surfaces for cell attachment. The voids interconnect, providing access to the cells throughout the interior of the particle. The material appears to be roughly 99.5% void volume, making the material very efficient in terms of the potential cell mass that can be grown per gram of microcarrier.

The morphogenically active fragments of 60A protein (comprising, e.g., Seq. ID NO. 2) described herein can be combined and dispersed in an appropriately modified tissue-specific matrix using any of the methods described below:

1. Ethanol Precipitation

Matrix is added to the morphogen dissolved in guanidine-HCl. Samples are vortexed and incubated at a low temperature. Samples are then further vortexed. Cold absolute ethanol is added to the mixture which is then stirred and incubated. After centrifugation (microfuge, high speed) the supernatant is discarded. The matrix is washed with cold concentrated ethanol in water and then lyophilized.

2. Acetonitrile Trifluoroacetic Acid Lyophilization

In this procedure, a morphogenically active fragment of 60A protein (comprising, e.g., Seq. ID NO. 2) in an acetonitrile trifluroacetic acid (ACN/TFA) solution is added to the carrier material. Samples are vigorously vortexed many times and then lyophilized.

3. Buffered Saline Lyophilization

A preparation of a morphogenically active fragment of 60A protein (comprising, e.g., Seq. ID NO. 2) in physiological saline also may be vortexed with the matrix and lyophilized to produce morphogenically active material.

Tissue morphogenesis requires a morphogenically permissive environment. Clearly, in fully-functioning healthy tissue that is not composed of a permanently renewing cell population, there must exist signals to prevent continued tissue growth. Thus, it is postulated that there exists a control mechanism, such as a feedback control mechanism, which regulates the control of cell growth and differentiation. In fact, it is known that both TGF-$\beta$, and MIS are capable of inhibiting cell growth when present at appropriate concentrations. In addition, using the bone model system it can be shown that osteogenic devices comprising a bone-derived carrier (matrix) that has been demineralized and guanidine-extracted to substantially remove the noncollagenous proteins does allow endochondral bone formation when implanted in association with an osteoinductive morphogen. If, however, the bone-derived carrier is not demineralized but rather is washed only in low salt, for example, induction of endochondral bone formation is inhibited, suggesting the presence of one or more inhibiting factors within the carrier.

III. EXAMPLES

Example 1

Recombinant Production of Morphogenic 60A Protein

The 60A proteins (comprising, e.g., Seq. ID NO. 2) useful in the methods and compositions of this invention may be purified from natural sources or produced using standard recombinant methodology. General considerations for the recombinant production of morphogens are described in U.S. Ser. No. 667,274 (abandoned in favor of CIP U.S. application Ser. No. 08/404,113, filed Mar. 14, 1995 and 752,764, (application Ser. No. 08/404,113, filed Mar. 14, 1995 the disclosures of which are incorporated hereinabove by reference.

A currently preferred protocol for producing 60A protein (comprising, e.g., Seq. ID NO. 2) uses cloning plasmids with commercially available promoters and selection marker sequences in the Drosophila S2 cell line, a Drosophila melanogaster cell line derived from late embryonic stages, as described below. A detailed description of the protocol can be found in Panganiban et al., (1990) *Mol. Cell. Biol.* 10:2669–2677 the disclosure of which is incorporated herein by reference. Briefly, the full length Drosophila 60A cDNA clone was incorporated into an expression plasmid that contained a metallothionein promoter and leader sequence and co-transfected into a host S2 cell with a selection plasmid (e.g., containing the marker gene dihydrofolate reductase for selection and amplication.) The expression promotor and selection sequences may be obtained commercially from, for example, from Clontech, Inc., Palo Alto, or the ATCC, Rockville, Md. (e.g.,from plasmid #37148).

Transfected cells were grown in M3 medium supplemented with 12.5% fetal cal serum (FCS, Gibco Laboratories) to which 2×10$^{-7}$M methotrexate (MTX) was added 3 days post transfection. On day 7, 4×10$^6$ cells from each transfection, together with 10$^6$ gamma-irradiated S2 feeder cells, were plated with 2 ml of 0.3% Noble agar. MTX-resistant cells then were serially subcultured for 74 days, subcultured once again, and transferred to small tissue culture flasks containing 3 ml media for 60A protein (comprising, e.g., Seq. ID NO. 2) induction with 500 $\mu$m CUSO$_4$. The 60A protein (comprising, e.g., Seq. ID NO. 2) expressed in the S2 system cells is produced as a processed mature disulfide-linked dimer and secreted into the medium as a soluble protein.

The recombinantly produced 60A protein (comprising, e.g., Seq. ID NO. 2) then was purified from the medium using two chromatography steps: S-sepharose (Sigma Chemical Co., St. Louis) and reverse phase HPLC (e.g., Aldrich Chemical Co., Milwaukee). A typical purification utilized 50 ml of medium containing 5% fetal calf serum. The media was diluted with 2 volumes of 9 M urea, 20 mM MES, pH 7.0 and applied to a 10 ml column of S-sepharose equilibrated with 6 M urea, 20 mM MES, pH 7.0, containing 50 mM $NaCl_2$. After washing with the equilibration buffer, step elution of bound protein was accomplished with the same buffer containing 100 and 300 mM $NaCl_2$. The 300 mM NaCl fraction then was sequentially dialysed against water and 30% acetonitrile/0.1% trifluoroacetic acid, and finally subjected to C18 reverse phase HPLC. Fractions containing morphogen (e.g., 60A protein (comprising, e.g., Seq. ID NO. 2)) were determined by immunoblot analysis (using 60A-specific polyclonal antibody) and Coomassie staining. Immunoreactive fractions then were pooled and the purity of 60A protein (comprising, e.g., Seq. ID NO. 2) determined by standard gel scanning methods. The concentration of protein was estimated by scanning the Coomassie-stained protein band in the gel at 580 nm in reference to a known amount of standard bovine serum albumin protein.

The purified protein is a processed mature disulfide-linked homodimer. The identity of the purified protein was confirmed by N-terminal sequencing and Western blot analysis using 60A-specific antisera.

Drosophila DPP (comprising, e.g., Seq. ID NO. 9) also was cloned and purified as described for 60A protein (comprising, e.g., Seq. ID NO. 2). DPP (comprising, e.g., Seq. ID NO. 9) was expressed and secreted as a processed mature disulfide-linked dimer which then bound to and accumulated on the petri dish surface. The DPP protein (comprising, e.g., Seq. ID NO. 9) that bound to plates was extracted with 200 mM $CaCl_2$/1% Tween-20/20 mM MES buffer pH 7.2, and purified on an S-Sepharose and C-18 column as described for 60A protein (comprising, e.g., Seq. ID NO. 2).

The identification of mature DPP (comprising, e.g., Seq. ID NO. 9) and 60A protein (comprising, e.g., Seq. ID NO. 2) was made by (1) N-terminal amino acid sequence analysis, (2) Western blot analysis using morphogen specific antisera, and (3) SDS-PAGE analysis under non-reduced and reduced conditions. Because of the homology at the C-terminal domains, the reaction of DPP (comprising, e.g., Seq. ID NO. 9) and 60A protein (comprising, e.g., Seq. ID NO. 2) with BMP-2 (CBMP2A (comprising, e.g., Seq. ID NO. 7)) and OP-1, (comprising, e.g., Seq. ID NO. 3) using antisera specific for these morphogens, was examined. Western blot analysis indicates DPP (comprising, e.g., Seq. ID NO. 9) reacts to BMP-2 antisera alone, and 60A protein (comprising, e.g., Seq. ID NO. 2) reacts with OP-1-specific antisera alone. The morphogen-specific antisera employed in the Western blots were produced by immunizing rabbits with the C-terminal domains of E. coli produced human BMP-2 and BMP4, for BMP-2-specific antisera, or E. coli produced OP-1 (comprising, e.g., Seq. ID NO. 3) (for OP-1-specific antibody), using standard immunology techniques. The antibody cross-reactivity data, together with the significant amino acid sequence homology, further suggests that 60A protein (comprising, e.g., Seq. ID NO. 2) likely may be the Drosophila homolog or species variant of OP1, and DPP (comprising, e.g., Seq. ID NO. 9), the homolog or the species variant of BMP2.

Example 2

Mitogenic Effect of 60A Protein 2.1 Mitogenic Effect of Morphogen on Rat and Human Osteoblasts The ability of 60A protein (comprising, e.g., Seq. ID NO. 2) to induce proliferation of osteoblasts may be determined in vitro using the following assay. In this and all examples involving osteoblast cultures, rat osteoblast-enriched primary cultures preferably are used. Although these cultures are heterogeneous in that the individual cells are at different stages of differentiation, the culture is believed to more accurately reflect the metabolism and function of osteoblasts in vivo than osteoblast cultures obtained from established cell lines. Unless otherwise indicated, all chemicals referenced are standard, commercially available reagents, readily available from a number of sources, including Sigma Chemical, Co., St. Louis; Calbiochem, Corp., San Diego and Aldrich Chemical Co., Milwaukee.

Rat osteoblast-enriched primary cultures are prepared by sequential collagenase digestion of newborn suture-free rat calvaria (e.g., from 1–2 day-old animals, Long-Evans strain, Charles River Laboratories, Wilmington, Mass.), following standard procedures, such as are described, for example, in Wong et al., (1975) *PNAS* 72:3167–3171. Rat osteoblast single cell suspensions then are plated onto a multi-well plate (e.g., a 24 well plate) at a concentration of 50,000 osteoblasts per well in alpha MEM (modified Eagle's medium, Gibco, Inc., Long Island) containing 10% FBS (fetal bovine serum), L-glutamine and penicillin/streptomycin. The cells are incubated for 24 hours at 37° C., at which time the growth medium is replaced with alpha MEM containing 1% FBS and the cells incubated for an additional 24 hours so that cells are in serum-deprived growth medium at the time of the experiment.

The cultured cells are divided into three groups: (1) wells which receive, for example, 0.1, 1.0, 10.0, 40 and 80.0 ng of 60A protein (comprising, e.g., Seq. ID NO. 2); (2) wells which receive 0.1, 1.0, 10.0 and 40 ng of a local-acting growth factor (e.g., TGF-β); and (3) the control group, which receive no growth factors. The cells then are incubated for an additional 18 hours after which the wells were pulsed with 2 $\mu$Ci/well of $^3$H-thymidine and incubated for six more hours. The excess label then is washed off with a cold solution of 0.15 M NaCl, and then 250 $\mu$l of 10% tricholoracetic acid added to each well and the wells incubated at room temperature for 30 minutes. The cells then are washed three times with cold distilled water, and lysed by the addition of 250 $\mu$l of 1% sodium dodecyl sulfate (SDS) for a period of 30 minutes at 37° C. The resulting cell lysates are harvested using standard means well known in the art, and the incorporation of $^3$H-thymidine into cellular DNA determined by liquid scintillation as an indication of mitogenic activity of the cells. In the experiment, 60A protein (comprising, e.g., Seq. ID NO. 2) stimulates $^3$H-thymidine incorporation into DNA, and thus promote osteoblast cell proliferation. By contrast, the effect of TGF-β is transient and biphasic. At high concentrations, TGF-β has no significant effect on osteoblast cell proliferation.

The in vitro effect of 60A protein (comprising, e.g., Seq. ID NO. 2) on osteoblast proliferation also can be tested on human primary osteoblasts (obtained from bone tissue of a normal adult patient and prepared as described above) and on human osteosarcoma-derived cell lines. In all cases 60A protein is anticipated to induce cell proliferation in accordance with the morphogen's ability to induce endochondral bone formation (see Example 7, below).

2.2 Progenitor Cell Stimulation

The ability of 60A protein (comprising, e.g., Seq. ID NO. 2) to stimulate the proliferation of progenitor cells also can be assayed readily in vitro using the following assay. Useful naive stem cells include pluripotential stem cells, which may be isolated from bone marrow or umbilical cord blood using conventional methodologies, (see, for example, Faradji et al., (1988) *Vox Sanq.*, 55 (3):133–138 or Broxmeyer et al., (1989) *PNAS* 86:3828–3832), as well as naive stem cells obtained from blood. Alternatively, embryonic cells (e.g., from a cultured mesodermal cell line) may be useful.

Another method for obtaining progenitor cells and for determining the ability of 60A protein (comprising, e.g., Seq. ID NO. 2) fragments to stimulate cell proliferation is to capture progenitor cells from an in vivo source. For example, a biocompatible matrix material able to allow the influx of migratory progenitor cells may be implanted at an in vivo site long enough to allow the influx of migratory progenitor cells. For example, a bone-derived, guanidine-extracted matrix, formulated as disclosed for example in Sampath et al. ((1983) *PNAS* 80:6591–6595), or U.S. Pat. No. 4,975,526, may be implanted into a rat at a subcutaneous site, essentially following the method of Sampath et al. After three days the implant is removed, and the progenitor cells associated with the matrix dispersed and cultured.

Progenitor cells, however obtained, then are incubated in vitro with a morphogenic 60A protein (comprising, e.g., Seq. ID NO. 2) fragment under standard cell culture conditions well described in the art and described hereinabove. In the absence of external stimuli, the progenitor cells do not, or only minimally, proliferate on their own in culture. However, progenitor cells cultured in the presence of a morphogenically active fragment of 60A protein (comprising, e.g., Seq. ID NO. 2) do proliferate. Cell growth can be determined visually or spectrophotometrically using standard methods well known in the art.

Example 3

Morphogen-Induced Cell Differentiation

3.1 Embryonic Mesenchyme Differentiation

Morphogenically active fragments of 60A protein (comprising, e.g., Seq. ID NO. 2) can be utilized to induce cell differentiation. The ability of 60A protein (comprising, e.g., Seq. ID NO. 2) to induce cell differentiation can be determined by culturing early mesenchymal cells in the presence of 60A protein (comprising, e.g., Seq. ID NO. 2) and then studying the histology of the cultured cells by staining with toluidine blue using standard cell culturing and cell staining methodologies well described in the art. For example, it is known that rat mesenchymal cells destined to become mandibular bone, when separated from the overlying epithelial cells at stage 11 and cultured in vitro under standard tissue culture conditions, e.g., in a chemically defined, serum-free medium, containing for example, 67% DMEM (Dulbecco's modified Eagle's medium), 22% F-12 medium, 10 mM Hepes pH 7, 2 mM glutamine, 50 µg/ml transferring, 25 µg/ml insulin, trace elements, 2 mg/ml bovine serum albumin coupled to oleic acid, with HAT (0.1 mM hypoxanthine, 10 µM aminopterin, 12 µM thymidine, will not continue to differentiate. However, if these same cells are left in contact with the overlying endoderm for an additional day, at which time they become stage 12 cells, they will continue to differentiate on their own in vitro to form chondrocytes. Further differentiation into obsteoblasts and, ultimately, mandibular bone, requires an appropriate local environment, e.g., a vascularized environment.

Stage 11 mesenchymal cells, cultured in vitro in the presence of 60A protein (comprising, e.g., Seq. ID NO. 2), e.g., 10–100 µg/ml, will continue to differentiate in vitro to form chondrocytes just as they continue to differentiate in vitro if they are cultured with the cell products harvested from the overlying endodermal cells. This experiment may be performed with different mesenchymal cells to assess the cell differentiation capability of different morphogenically active fragments of 60A protein (comprising, e.g., Seq. ID NO. 2).

As another example of morphogen-induced cell differentiation, the ability of 60A proteins (comprising, e.g., Seq. ID NO. 2) to induce osteoblast differentiation may be evaluated in vitro using primary osteoblast cultures or osteoblast-like cells lines and assaying for a variety of-bone cell markers that are specific markers for the differentiated osteoblast phenotype, e.g., alkaline phosphatase activity, parathyroid hormone-mediated cyclic AMP (cAMP) production, osteocalcin synthesis, and enhanced mineralization rates.

3.2 Alkaline Phosphatase Induction of Osteoblasts by 60A Protein

The cultured cells in serum-free medium are incubated with, for example, 0.1, 1.0, 10.0, 40.0 or 80.0 ng 60A protein (comprising, e.g., Seq. ID NO. 2)/ml medium; or TGF-$\beta$ at 0.1, 1.0, 10.0, 40.0 or 80.0 ng/ml medium for 72 hours. After the incubation period the cell layer is extracted with 0.5 ml of 1% Triton X-100. The resultant cell extract is centrifuged, 100 µl of the extract is added to 90 µl of paranitrosophenylphosphate (PNPP)/glycerine mixture and incubated for 30 minutes in a 37° C. water bath and the reaction stopped with 100 µl NaOH. The samples then are run through a plate reader (e.g., Dynatech MR700 plate reader, and absorbance measured at 400 nm, using p-nitrophenol as a standard) to determine the presence and amount of alkaline phosphate activity. Protein concentrations are determined by the Biorad method. Alkaline phosphatase activity is calculated in units/µg protein, where 1 unit=1 nmol p-nitrophenol liberated/30 minutes at 37° C.

60A protein (comprising, e.g., Seq. ID NO. 2) alone stimulates the production of alkaline phosphatase in osteoblasts, and thus promotes the growth and expression of the osteoblast differentiated phenotype.

The long term effect of 60A (comprising, e.g., Seq. ID NO. 2) morphogen on the production of alkaline phosphatase by rat osteoblasts also may be demonstrated as follows.

Rat osteoblasts are prepared and cultured in multi-well plates as described above. In this example six sets of 24 well plates are plated with 50,000 rat osteoblasts per well. The wells in each plate, prepared as described above, then are divided into three groups: (1) those which receive, for example, 1 ng of 60A protein (comprising, e.g., Seq. ID NO. 2) per ml of medium; (2) those which receive 40 ng of 60A protein (comprising, e.g., Seq. ID NO. 2) per ml of medium; and (3) those which received 80 ng of 60A protein (comprising, e.g., Seq. ID NO. 2) per ml of medium. Each plate then is incubated for different lengths of time: 0 hours (control time), 24 hours, 48 hours, 96 hours, 120 hours and 144 hours. After each incubation period, the cell layer is extracted with 0.5 ml of 1% Triton X-100. The resultant cell extract is centrifuged, and alkaline phospatase activity determined as for Example 3.1, using paranitrosophenylphosphate (PNPP). 60A protein (comprising, e.g., Seq. ID NO. 2) stimulates the production of alkaline phosphatase in osteoblasts in dose-dependent manner so that increasing doses of 60A (comprising, e.g., Seq. ID NO. 2) further increase the level of alkaline phosphatase production, and moreover, the 60A-stimulated elevated levels of alkaline phosphatase in the treated osteoblasts is anticipated to last for an extended period of time.

3.3 60A Protein Induction of PTH-Mediated cAMP

The effect of a 60A (comprising, e.g., Seq. ID NO. 2) on parathyroid hormone-mediated cAMP production in rat osteoblasts in vitro may be demonstrated as follows.

Rat osteoblasts are prepared and cultured in a multiwell plate as described above. The cultured cells then are divided into three groups: (1) wells which receive, for example, 1.0, 10.0 and 40.0 ng 60A protein (comprising, e.g., Seq. ID NO. 2) ml medium); (2) wells which receive for example, TGF-β, at 0.1, 1.0, and 5.0 ng/ml medium); and (3) a control group which receives no growth factors. The plate is then incubated for another 72 hours. At the end of the 72 hours the cells are treated with medium containing 0.5% bovine serum albumin (BSA) and 1 mM 3-isobutyl-1-methylxanthine for 20 minutes followed by the addition into half of the wells of human recombinant parathyroid hormone (hPTH, Sigma, St. Louis) at a concentration of 200 ng/ml for 10 minutes. The cell layer then is extracted from each well with 0.5 ml of 1% Triton X-100. The cAMP levels then are determined using a radioimmunoassay kit (e.g., Amersham, Arlington Heights, Ill.). 60A protein (comprising, e.g., Seq. ID NO. 2) alone stimulates an increase in the PTH-mediated cAMP response, and thus promotes the growth and expression of the osteoblast differentiated phenotype.

3.4 60A Protein Induction of Osteocalcin Production

Osteocalcin is a bone-specific protein synthesized by osteoblasts which plays an integral role in the rate of bone mineralization in vivo. Circulating levels of osteocalcin in serum are used as a marker for osteoblast activity and bone formation in vivo. Induction of osteocalcin synthesis in osteoblast-enriched cultures can be used to demonstrate 60A (comprising, e.g., Seq. ID NO. 2) morphogenic efficacy in vitro.

Rat osteoblasts are prepared and cultured in a multi-well plate as above. In this experiment the medium is supplemented with 10% FBS, and on day 2, cells are fed with fresh medium supplemented with fresh 10 mM β-glycerophosphate (Sigma, Inc.). Beginning on day 5 and twice weekly thereafter, cells are fed with a complete mineralization medium containing all of the above components plus fresh L(+)-ascorbate, at a final concentration of 50 μg/ml medium. 60A protein then is added to the wells directly, e.g., in 50% acetonitrile (or 50% ethanol) containing 0.1% trifluoroacetic acid (TFA), at no more than 5 μl morphogen/ml medium. Control wells receive solvent vehicle only. The cells then are re-fed and the conditioned medium sample diluted 1:1 in standard radioimmunoassay buffer containing standard protease inhibitors and stored at −20° C. until assayed for osteocalcin. Osteocalcin synthesis is measured by standard radioimmunoassay using a commercially available osteocalcin-specific antibody.

Mineralization is determined on long term cultures (13 day) using a modified von Kossa staining technique on fixed cell layers: cells are fixed in fresh 4% paraformaldehyde at 23° C. for 10 mn, following rinsing cold 0.9% NaCl. Fixed cells then are stained for endogenous alkaline phosphatase at pH 9.5 for 10 min, using a commercially available kit (Sigma, Inc.) Purple stained cells then are dehydrated with methanol and air dried. after 30 min incubation in 3% $AgNO_3$ in the dark, $H_2O$-rinsed samples are exposed for 30 sec to 254 nm UV light to develop the black silver-stained phosphate nodules. Individual mineralized foci (at least 20 μm in size) are counted under a dissecting microscope and expressed as nodules/culture.

60A protein (comprising, e.g., Seq. ID NO. 2) stimulates osteocalcin synthesis in osteoblast cultures. The increased osteocalcin synthesis in response to 60A protein (comprising, e.g., Seq. ID NO. 2) is expected to be dose dependent and to show a significant increase over the basal level after 13 days of incubation. The enhanced osteocalcin synthesis also can be confirmed by detecting the elevated osteocalcin mRNA message (20-fold increase) using a rat osteocalcin-specific probe. In addition, the increase in osteoclacin synthesis is expected to correlate with increased mineralization in long term osteoblast cultures as determined by the appearance of mineral nodules 60A protein (comprising, e.g., Seq. ID NO. 2) is expected to increase the initial mineralization rate about 20-fold compared to untreated cultures.

3.5 Morphogen-Induced CAM Expression

The morphogens described herein induce CAM expression, particularly N-CAM expression, as part of their induction of morphogenesis (see copending U.S. Ser. No. 922,813application Ser. No. 08/260,674, filed Jun. 16, 1994). CAMs are morphoregulatory molecules identified in all tissues as an essential step in tissue development. N-CAMs, which comprise at least 3 isoforms (N-CAM-180, N-CAM-140 and N-CAM-120, where "180", "140" and "120" indicate the apparent molecular weights of the isoforms as measured by polyacrylamide gel electrophoresis) are expressed at least transiently in developing tissues, and permanently in nerve tissue. Both the N-CAM-180 and N-CAM-140 isoforms are expressed in both developing and adult tissue. The N-CAM-120 isoform is found only in adult tissue. Another neural CAM is L1.

The ability of 60A proteins (comprising, e.g., Seq. ID NO. 2) to stimulate CAM expression can be demonstrated using the following protocol, using NG108–15 cells. NG108–15 is a transformed hybrid cell line (neuroblastoma x glioma, America Type Tissue Culture (ATCC), Rockville, Md.), exhibiting a morphology characteristic of transformed embryonic neurons. As described in Example 4, below, untreated NG108-15 cells exhibit a fibroblastic, or minimally differentiated, morphology and express only the 180 and 140 isoforms of N-CAM normally associated with a developing cell. Following morphogen treatment these cells exhibit a morphology characteristic of adult neurons and express enhanced levels of all three N-CAM isoforms.

In this example NG108–15 cells are cultured for 4 days in the presence of increasing concentrations of 60A protein (comprising, e.g., Seq. ID NO. 2) using standard culturing procedures, and standard Western blots performed on whole cell extracts. N-CAM isoforms are detected with an antibody which crossreacts with all three isoforms, mAb H28.123, obtained from Sigma Chemical Co., St. Louis, the different isoforms being distinguishable by their different mobilities on an electrophoresis gel. Control NG108–15 cells (untreated) express both the 140 kDa and the 180 kDa isoforms, but not the 120 kDa, as determined by Western blot analyses using up to 100 μg of protein. Treatment of NG108–15 cells with 60A protein (comprising, e.g., Seq. ID NO. 2) results in a dose-dependent increase in the expression of the 180 kDa and 140 kDa isoforms, as well as the induction of the 120 kDa isoform induced. In addition, CAM expression correlates with cell aggregation as well as morphology, as determined by histology. Morphogen treatment also induces expression of another neural CAM, L1.

Example 4

60A Protein-Induced Redifferentiation of Transformed Phenotype

The 60A protein (comprising, e.g., Seq. ID NO. 2) morphogens described herein also can induce redifferentiation of transformed cells to a morphology characteristic of untransformed cells. The examples provided below detail morphogen-induced redifferentiation of a transformed human cell line of neuronal origin (NG108–15); as well as mouse neuroblastoma cells (N1E-115), and human embryo carcinoma cells, to a morphology characteristic of untransformed cells.

As described above, NG108–15 is a transformed hybrid cell line produced by fusing neuroblastoma x glioma cells (obtained from ATTC, Rockville, Md.), and exhibiting a morphology characteristic of transformed embryonic neurons, e.g., having a fibroblastic morphology. Specifically, the cells have polygonal cell bodies, short, spike-like processes and make few contacts with neighboring cells (see copending U.S. Ser. No. 922,813 application Ser. No. 08/860,674, filed Jun. 16, 1994). Incubation of NG108–15 cells, cultured in a chemically defined, serum-free medium, with 0.1 to 300 ng/ml of morphogen (e.g; OP-1 (comprising, e.g., Seq. ID NO. 3)) for four hours induces an orderly, dose-dependent change in cell morphology.

In the example, NG108–15 cells are subcultured on poly-L-lysine coated 6 well plates. Each well contains 40–50,000 cells in 2.5 ml of chemically defined medium. On the third day, 2.5 $\mu$l of morphogen (e.g., 60A protein (comprising, e.g., Seq. ID NO. 2)) in 60% ethanol containing 0.025% trifluoroacetic is added to each well. Morphogenic 60A protein (comprising, e.g., Seq. ID NO. 2) of varying concentrations may be tested (typically, concentration ranges of 0–300 ng/ml are tested). The media is changed daily with new aliquots of morphogen. Morphogenic 60A protein (comprising, e.g., Seq. ID NO. 2) induces a dose-dependent redifferentiation of the transformed cells, including a rounding of the soma, an increase in phase brightness, extension of the short neurite processes, and other significant changes in the cellular ultrastructure. After several days treated cells will begin to form epithelioid sheets that then become highly packed, multi-layered aggregates, as determined visually by microscopic examination.

Moreover, morphogen-induced redifferentiation occurs without any associated changes in DNA synthesis, cell division, or cell viability, making it unlikely that the morphologic changes are secondary to cell differentiation or a toxic effect of the morphogen. In addition, the morphogen-induced redifferentiation does not inhibit cell division, as determined by $^3$H-thymidine uptake, unlike other molecules which have been shown to stimulate differentiation of transformed cells, such as butyrate, DMSO, retanoic acid or Forskolin in analogous experiments. Thus, 60A protein (comprising, e.g., Seq. ID NO. 2) maintains cell stability and viability after inducing redifferentiation.

The 60A protein (comprising, e.g., Seq. ID NO. 2) morphogens described herein accordingly provide useful therapeutic agents for the treatment of neoplasias and neoplastic lesions of the nervous system, particularly in the treatment of neuroblastomas, including retinoblastomas, and gliomas.

As yet another, related example, the ability of 60A proteins (comprising, e.g., Seq. ID NO. 2) to induce the "redifferentiation" of transformed human cells may be demonstrated. Specifically, the effect of 60A protein (comprising, e.g., Seq. ID NO. 2) fragments on human EC cells (embryo carcinoma cells, e.g., NTERA-Z CL.D1, ATCC, Rockville, Md.) may be determined. In the absence of an external stimulant, these cells can be maintained as undifferentiated stem cells, and can be induced to grow in serum free media (SFM). In the absence of treatment with a morphogen, the cells proliferate rampantly and are anchorage-independent. In the presence of morphogen EC cells grow as flattened cells, becoming anchorage dependent and forming aggregates. In addition, growth rate is reduced approximately 10 fold. Ultimately, the cells are induced to differentiate. In the example, varying concentrations of 60A protein (comprising, e.g., Seq. ID NO. 2) (e.g., 0–300 ng/ml) are added daily to cultured cells (e.g., 40–50,000 cells in 2.5 ml chemically defined medium), and the effects of treatment determined by visual examination. 60A protein (comprising, e.g., Seq. ID NO. 2) stimulates redifferentiation of these cells to a morphology characteristic of untransformed embryo cells.

Example 5

Maintenance of Phenotype

Morphogenically active fragments of 60A protein (comprising, e.g., Seq. ID NO. 2) also may be used to maintain a cell's differentiated phenotype. This application is particularly useful for inducing the continued expression of phenotype in senescent or quiescent cells.

5.1 In vitro Model for Phenotypic Maintenance

The phenotypic maintenance capability of morphogens is assessed readily. A number of differentiated cells become senescent or quiescent after multiple passages in vitro under standard tissue culture conditions such well described in the art, e.g., *Culture of Animal Cells: A Manual of Basic Techniques* (R. Freshney, ed., Wiley, 1987). However, if these cells are cultivated in vitro in association with a morphogen such as 60A protein (comprising, e.g., Seq. ID NO. 2), cells are stimulated to maintain expression of their phenotype through multiple passages. For example, the alkaline phosphatase activity of cultured osteoblasts, such as cultured osteosarcoma cells and calvaria cells, is significantly reduced after multiple passages in vitro. However, if the cells are cultivated in the presence of a morphogenically active fragment of 60A protein (comprising, e.g., Seq. ID NO. 2), alkaline phosphatase activity is maintained over extended periods of time. Similarly, phenotypic expression of myocytes also is maintained in the presence of a morphogen. In the experiment, osteoblasts are cultured as described in Example 2. The cells are divided into groups, incubated with varying concentrations of 60A protein (comprising, e.g., Seq. ID NO. 2) (e.g., 0–300 ng/ml) and passaged multiple times (e.g., 3–5 times) using standard methodology. Passaged cells then are tested for alkaline phosphatase activity, as described in Example 3 as an indication of differentiated cell metabolic function. Osteoblasts cultured in the absence of 60A protein (comprising, e.g., Seq. ID NO. 2) have a reduced alkaline phosphatase activity, as compared to 60A protein-treated cells.

5.2 In Vivo Model for Phenotypic Maintenance

Phenotypic maintenance capability also may be assessed in vivo, using a rat model for osteoporosis, as disclosed in the copending U.S. Ser. No. 752,857, application Ser. No. 08/155,343, filed Nov. 15, 1993, filed Aug. 30, 1991, and [U.S. Ser. No. 923,780 application Ser. No. 08/432,883, filed May 2, 1995] incorporated herein above by reference. As described therein, Long Evans female rats (Charles River Laboratories, Wilmington, Mass.) are ovariectomized using standard surgical techniques, to produce an osteoporotic condition resulting from decreased estrogen production. Eight days after ovariectomy, rats are systemically provided with phosphate buffered saline (PBS) or morphogen, (e.g., 60A protein, 2–20 µg) for 21 days. The rats then are sacrificed and serum alkaline phosphatase levels, serum calcium levels, and serum osteocalcin levels are determined, using standard methodologies as described therein and above. Elevated levels of osteocalcin and alkaline phosphatase are anticipated in the rats treated with an effective amount of a morphogenic 60A protein (comprising, e.g., Seq. ID NO. 2). Moreover, histomorphometric analysis on the tibial diasypheal bone shows improved bone mass in 60A protein-treated animals as compared with untreated, ovariectomized rats. In fact, the bone mass of 60A protein-animals is comparable to that of the sham-operated (e.g., nonovarectomized) rats.

Example 6

Proliferation of Progenitor Cell Populations

Progenitor cells may be stimulated to proliferate in vivo or ex vivo. The cells may be stimulated in vivo by injecting or otherwise providing a sterile preparation containing the morphogenically active fragment of 60A protein (comprising, e.g., Seq. ID NO. 2) into the individual. For example, the hemopoietic pluripotential stem cell population of an individual may be stimulated to proliferate by injecting or otherwise providing an appropriate concentration of the morphogenically active fragment of 60A protein (comprising, e.g., Seq. ID NO. 2) to the individual's bone marrow.

Progenitor cells may be stimulated ex vivo by contacting progenitor cells of the population to be enhanced with a morphogenically active fragment of 60A protein under (comprising, e.g., Seq. ID NO. 2) sterile conditions at a concentration and for a time sufficient to stimulate proliferation of the cells. Suitable concentrations and stimulation times may be determined empirically, essentially following the procedure described in Example 2, above. A morphogen concentration of between about 0.1–100 ng/ml and a stimulation period of from about 10 minutes to about 72 hours, or, more generally, less than about 24 hours, typically should be sufficient to stimulate a cell population of about $10^4$ to $10^6$ cells. The stimulated cells then are provided to the individual as, for example, by injecting the cells to an appropriate in vivo locus. Suitable biocompatible progenitor cells may be obtained by any of the methods known in the art or described hereinabove.

Example 7

Regeneration of Damaged or Diseased Tissue

The morphogenically active fragments of Drosophila 60A protein (comprising, e.g., Seq. ID NO. 2) may be used to repair diseased or damaged mammalian tissue. The tissue to be repaired preferably is assessed first, and excess necrotic or interfering scar tissue removed as needed, e.g., by ablation or by surgical, chemical or other methods known in the medical arts.

The 60A protein (comprising, e.g., Seq. ID NO. 2) then may be provided directly to the tissue locus as part of a sterile, biocompatible composition, either by surgical implantation or injection. The morphogen also may be provided systemically, as by oral or parenteral administration. Alternatively, a sterile, biocompatible composition containing progenitor cells stimulated by a morphogenically active fragment of 60A protein (comprising, e.g., Seq. ID NO. 2) may be provided to the tissue locus. The existing tissue at the locus, whether diseased or damaged, provides the appropriate matrix to allow the proliferation and tissue-specific differentiation of progenitor cells. In addition, a damaged or diseased tissue locus, particularly one that has been further assaulted by surgical means, provides a morphogenically permissive environment. Systemic provision of a morphogenically active fragment of 60A protein (comprising, e.g., Seq. ID NO. 2) will be sufficient for certain applications (e.g., in the treatment of osteoporosis and other disorders of the bone remodeling cycle, as an example).

In some circumstances, particularly where tissue damage is extensive, the tissue may not be capable of providing a sufficient matrix for cell influx and proliferation. In these instances, it may be necessary to provide the 60A protein (comprising, e.g., Seq. ID NO. 2) or progenitor cells stimulated by 60A protein (comprising, e.g., Seq. ID NO. 2) to the tissue locus in association with a suitable, biocompatible, formulated matrix, prepared by any of the means described below. The matrix preferably is in vivo biodegradable. The matrix also may be tissue-specific and may comprise porous particles having dimensions within the range of 70–850 µm, most preferably 150–420 µm.

The morphogenic 60A protein (comprising, e.g., Seq. ID NO. 2) also may be used to prevent or substantially inhibit immune/inflammatory response mediated tissue damage and scar tissue formation following an injury. 60A protein (comprising, e.g., Seq. ID NO. 2) is provided to a newly injured tissue locus, to induce tissue morphogenesis at the locus, preventing the aggregation of migrating fibroblasts into non-differentiated connective tissue. The 60A protein (comprising, e.g., Seq. ID NO. 2) fragment preferably is provided as a sterile pharmaceutical preparation injected into the tissue locus within five hours of the injury.

Below are several examples, describing protocols for assessing 60A protein-induced tissue morphogenesis in bone, liver, nerve, dentin, cementum and periodontal ligament.

7.1 60A Protein-Induced Bone Morphogenesis

A particularly useful mammalian tissue model system for demonstrating and evaluating the morphogenic activity of a protein is the endochondral bone tissue morphogenesis model known in the art and described, for example, in U.S. Pat. No. 4,968,590 and incorporated herein by reference. The ability to induce endochondral bone formation includes the ability to induce the proliferation and subsequent differentiation of progenitor cells into chondroblasts and osteoblasts, the ability to induce cartilage matrix formation, cartilage calcification, and bone remodeling, and the ability to induce formation of an appropriate vascular supply and hematopoeitic bone marrow differentiation.

The local environment in which the morphogenic material is placed is important for tissue morphogenesis. As used herein, "local environment" is understood to include the tissue structural matrix and the environment surrounding the tissue. For example, in addition to needing an appropriate anchoring substratum for their proliferation, the cells stimulated by morphogens need signals to direct the tissue-specificity of their differentiation. These signals vary for the different tissues and may include cell surface markers. In addition, vascularization of new tissue requires a local environment which supports vascularization.

The following sets forth various procedures for evaluating the in vivo morphogenic utility of the morphogenically active fragments of 60A protein (comprising, e.g., Seq. ID NO. 2) and compositions thereof. The fragments and compositions may be injected or surgically implanted in a mammal, following any of a number of procedures well known in the art. For example, surgical implant bioassays may be performed essentially following the procedure of Sampath et al. (1983) *PNAS* 80:6591–6595 and U.S. Pat. No. 4,968,590.

Histological sectioning and staining is preferred to determine the extent of morphogenesis in vivo, particularly in tissue repair procedures. Excised implants are fixed in Bouins Solution, embedded in paraffin, and cut into 6–8 μm sections. Staining with toluidine blue or hemotoxylin/eosin demonstrates clearly the ultimate development of the new tissue. Twelve day implants are usually sufficient to determine whether the implants contain newly induced tissue.

Successful implants exhibit a controlled progression through the stages of induced tissue development allowing one to identify and follow the tissue-specific events that occur. For example, in endochondral bone formation the stages include: (1) leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoclast and the commencement of bone remodeling and dissolution of the implanted matrix on days twelve to eighteen; and (8) hematopoietic bone marrow differentiation in the resulting ossicles on day twenty-one.

In addition to histological evaluation, biological markers may be used as markers for tissue morphogenesis. Useful markers include tissue-specific enzymes whose activities may be assayed (e.g., spectrophotometrically) after homogenization of the implant. These assays may be useful for quantitation and for rapidly obtaining an estimate of tissue formation after the implants are removed from the animal. For example, alkaline phosphatase activity may be used as a marker for osteogenesis.

Incorporation of systemically provided morphogenic fragments of 60A protein (comprising, e.g., Seq. ID NO. 2) may be followed using tagged fragments (e.g., radioactively labelled) and determining their localization in the new tissue, and/or by monitoring their disappearance from the circulatory system using a standard labeling protocol and pulse-chase procedure. The 60A protein (comprising, e.g., Seq. ID NO. 2) also may be provided with a tissue-specific molecular tag, whose uptake may be monitored and correlated with the concentration of the 60A protein (comprising, e.g., Seq. ID NO. 2) fragment provided. As an example, ovary removal in female rats results in reduced bone alkaline phosphatase activity and renders the rats predisposed to osteoporosis (as described in Example 5). If the female rats now are provided with a 60A protein (comprising, e.g., Seq. ID NO. 2), a reduction in the systemic concentration of calcium may be seen, which correlates with the presence of the provided 60A protein (comprising, e.g., Seq. ID NO. 2) and which is anticipated to correspond with increased alkaline phosphatase activity.

In this example, the recombinantly produced mature disulfide-linked homodimers of two Drosophila morphogens, DPP (comprising, e.g., Seq. ID NO. 9) and 60A proteins (comprising, e.g., Seq. ID NO. 2), were evaluated for their capacity to induce new endochondral bone formation in mammals using the rat subcutaneous bone induction model. As disclosed herein, both Drosophila proteins, DPP (comprising, e.g., Seq. ID NO. 9) and 60A protein (comprising, e.g., Seq. ID NO. 2), can induce the formation of new cartilage, bone and bone marrow at non-bony sites in mammals.

Purified, recombinant DPP (comprising, e.g., Seq. ID NO. 9) and 60A gene (comprising, e.g., Seq. ID NO. 2) products, produced as described in Example 1, above, then were combined in varying concentrations with rat collagen carrier and assayed for bone forming activity in rats as described above and in the art.

Briefly, DPP (comprising, e.g., Seq. ID NO. 9) or 60A protein (comprising, e.g., Seq. ID NO. 2) was reconstituted with rat collagen carrier by the 50% acetonitrile/0.1% TFA lyophilization method as described. In this example, 25 mg of 4 M guanidine HCl-extracted demineralized rat collagenous matrix (rat collagen carrier) was added to varying concentrations of protein dissolved in 200 μl of 50% acetonitrile/0.1% TFA, vortexed and then lyophilized. Rat collagen carrier alone was the negative control and intact demineralized bone matrix was the positive control. The day of implantation was designated as day 0 of the assay. Implants were removed on day 12 and bone forming activity in the implants was monitored by the specific activity of alkaline phosphatase and calcium content as described above. Values are the average of four to six observations from two to three rats. Table III evaluates the bone forming activity of 60A protein, DPP and OP. As can be seen, all three morphogens induce alkaline phosphatase activity and inherent calcium content.

The effect also was evaluated by histology. For histological examination, implants were fixed in Bouin's Solution, embedded in plastic medium, cut into one-micrometer sections and stained by toluidine blue.

Table III, below, catalogs the histology results of 60A protein (comprising, e.g., Seq. ID NO. 2) and DPP (comprising, e.g., Seq. ID NO. 9) induced endochondral bone formation. Bone formation was calculated as described in U.S. Pat. No. 4,968,590. Specifically, one bone forming unit represents the amount of protein needed for half maximal bone forming activity of the implant on day 12. The bone forming activity elicited by intact bone matrix is considered to be the maximal bone differentiation activity for comparison purposes in this assay. As is evident from the histology results, extensive bone formation and bone remodeling can be seen throughout the micrograph in a 60A protein (comprising, e.g., Seq. ID NO. 2) implant. Similar results were obtained using DPP implants, indicating that morphogens present in Drosophila induce de novo tissue regeneration in mammals.

TABLE III

BONE INDUCING ACTIVITY BY RECOMBINANT DPP AND 60A

| | Protein Concentration (ng/implant) (25 mg) | Alkaline Phosphatase U/mg protein | Calcium Content μg/mg tissue | Histology* |
|---|---|---|---|---|
| (comprising, eq., Seq. ID No. 9) | — | 0.06 | | — |
| | 480 | 1.43 | N.D | +++ |
| DPP | 1440 | 1.48 | N.D | +++ |
| 60A | — | | | — |
| (comprising, eq, Seq ID No. 2) | 400 | N.D | 9.75 | ++ |
| | 800 | N.D | 15.20 | +++ |
| | 1600 | N.D | 19.60 | +++ |

*histology observed on day 12
++ moderate bone formation
+++ excellent bone formation
N.D - Not determined 7.2 Morphogen-Induced Liver Regeneration As another example, a method for inducing morphogenesis of substantially injured liver tissue following a partial hepatectomy utilizing a morphogenic 60A protein (comprising, e.g., Seq. ID NO. 2) is presented. Variations on this general protocol may be used to test morphogen activity of 60A protein (comprising, e.g., Seq. ID NO. 2) fragments in other different tissues. The general method involves excising an essentially nonregenerating portion of a tissue and providing the morphogenic 60A protein (comprising, e.g., Seq. ID NO. 2), preferably as a soluble pharmaceutical preparation to the excised tissue locus, closing the wound, and examining the site at a future date. Like bone, liver has a potential to regenerate upon injury during post-fetal life.

The morphogenic 60A protein (comprising, e.g., Seq. ID NO. 2), e.g., 1 mg/ml, in a biocompatible solution, for example, (e.g., a purified recombinant mature form, is solubilized in 50% ethanol (or compatible solvent) containing 0.1% trifluoroacetic acid (or compatible acid). Alternatively, the mature protein may be solubilized by association with a pro domain. The injectable 60A protein (comprising, e.g., Seq. ID NO. 2) solution is prepared, e.g., by diluting one volume of 66A protein (comprising, e.g., Seq. ID NO. 2) solvent-acid stock solution with 9 volumes of 0.2% rat serum albumin in sterile PBS (phosphate-buffered saline).

In the experiment, growing rats or aged rats (e.g., Long Evans, Charles River Laboratories, Wilmington) are anesthetized by using ketamine. Two of the liver lobes (left and right) are cut out (approximately ⅓ of the lobe) and the 60A protein (comprising, e.g., Seq. ID NO. 2) is injected locally at multiple sites along the cut ends. The amount of 60A protein (comprising, e.g., Seq. ID NO. 2) injected may be, e.g., 100 $\mu$g in 1000 $\mu$l of PBS/RSA (phosphate buffered saline/rat serum albumin) injection buffer. Placebo samples are injection buffer only. In experimental assays, five rats in each group preferably are used. The wound is closed and the rats are allowed to eat normal food and drink tap water.

After 12 days, the rats are sacrificed and liver regeneration is observed visually, to evaluate the effects of the 60A protein (comprising, e.g., Seq. ID NO. 2) on liver regeneration most effectively. The 60A protein fragment-injected group shows, e.g., complete liver tissue regeneration with no sign remaining of any cut in the liver. By contrast, the control group into which only PBS is injected shows only minimal regeneration with the incision remaining in the sample. Previous experiments with other morphogens (e.g., OP-1 (comprising, e.g., Seq. ID NO. 3)) show these morphogens alone induce liver tissue regeneration.

7.3 Morphogen-Induced Dentin, Cementum and Periodontal Ligament Regeneration

As still another example, the ability of a morphogenically active fragmet of 60A protein (comprising, e.g., Seq. ID NO. 2) to induce dentinogenesis also may be demonstrated. To date, the unpredictable response of dental pulp tissue to injury is a basic clinical problem in dentistry. Cynomolgus monkeys are chosen as primate models as monkeys are presumed to be more indicative of human dental biology than models based on lower non-primate mammals.

Using standard dental surgical procedures, small areas (e.g., 2 mm) of dental pulps are surgically exposed by removing the enamel and dentin immediately above the pulp (by drilling) of sample teeth, performing a partial amputation of the coronal pulp tissue, inducing hemostasis, application of the pulp treatment, and sealing and filling the cavity by standard procedures.

Pulp treatments used may include: a morphogenically active fragment of 60A protein (comprising, e.g., Seq. ID NO. 2) dispersed in a carrier matrix; carrier matrix alone, and no treatment. Twelve teeth per animal (four for each treatment) are prepared, and two animals are used. At four weeks, teeth are extracted and processed histologically for analysis of dentin formation, and/or ground to analyze dentin mineralization. The effect of a fragment of 60A protein (comprising, e.g., Seq. ID NO. 2) on osteodentin reparation may be observed visually by comparing control samples treatment (PBS) with 60A protein (comprising, e.g., Seq. ID NO. 2) or DPP (comprising, e.g., Seq. ID NO. 9). 60A protein (comprising, e.g., Seq. ID NO. 2) plus a carrier matrix induces formation of reparative or osteodentin bridges on surgically exposed healthy dental pulps. By contrast, pulps treated with carrier matrix alone, do not to form reparative dentin.

Similarly, implanting demineralized teeth and 60A protein (comprising, e.g., Seq. ID NO. 2) into surgically prepared canine tooth sockets are anticipated to stimulate cementum and periodontal ligament formation, as well as new bone tissue, as described in U.S. Ser. No. application Ser. No. 08/155,343, filed Nov. 15, 1993, filed herewith, the disclosure of which is incorporated herein by reference.

7.4 Morphogen-Induced Nerve Tissue Repair

As yet another example, the induction of regenerative effects on central nervous system (CNS) repair, by a morphogenically active fragment of 60A protein, may be demonstrated using a rat brain stab model. Briefly, male Long Evans rats are anesthetized and the head area prepared for surgery. The calvariae is exposed using standard surgical procedures and a hole drilled toward the center of each lobe using a 0.035K wire, just piercing the calvariae. 25 $\mu$l solutions containing either morphogen (e.g., 60A protein (comprising, e.g., Seq. ID NO. 2), 25 $\mu$g in PBS) or PBS alone then is provided to each of the holes by Hamilton syringe. Solutions are delivered to a depth approximately 3 mm below the surface, into the underlying cortex, corpus callosum and hippocampus. The skin then is sutured and the animal allowed to recover.

Three days post surgery, rats are sacrificed by decapitation and their brains processed for sectioning. Scar tissue formation is evaluated by immunofluoresence staining for glial fibrillary acidic protein, a marker protein for glial scarring, to qualitatively determine the degree of scar formation. Sections also are probed with 60A protein-specific antibody to determine the presence of the protein. Reduced levels of glial fibrillary acidic protein are seen in the tissue sections of animals treated with 60A protein (comprising, e.g., Seq. ID NO. 2) evidencing the ability of the morphogen to inhibit glial scar formation, thereby stimulating nerve regeneration.

The ability of 60A protein (comprising, e.g., Seq. ID NO. 2) to stimulate peripheral nervous system axonal growth over extended distances may be demonstrated using the following model. Neurons of the peripheral nervous system can sprout new processes on their own following injury, but without guidance these sproutings typically fail to connect appropriately and die. Where the break is extensive, e.g., greater than 5 or 10 mm, regeneration is poor or nonexistent. Previous experiments with other morphogens, e.g., OP-1, (comprising, e.g., Seq. ID NO. 3) show that morphogens stimulate peripheral nervous system axonal growth over extended distances, allowing repair and regeneration of damaged peripheral neural pathways.

In this example 60A protein (comprising, e.g., Seq. ID NO. 2) stimulation of nerve regeneration is assessed using the rat sciatic nerve model. The rat sciatic nerve can regenerate spontaneously across a 5 mm gap, and occasionally across a 10 mm gap, provided that the severed ends are inserted in a saline-filled nerve guidance channel. In this experiment, nerve regeneration across at least a 12 mm gap is tested.

Adult female Sprague-Dawley rats (Charles River Laboratories, Inc.) weighing 230–250 g are anesthetized with intraperitoneal injections of sodium pentobarbital (35 mg/kg body weight). A skin incision is made parallel and just posterior to the femur. The avascular intermuscular plane between vastus lateralis and hamstring muscles are entered and followed to the loose fibroareolar tissue surrounding the sciatic nerve. The loose tissue is divided longitudinally thereby freeing the sciatic nerve over its full extent without devascularizing any portion. Under a surgical microscope the sciatic nerves are transected with microscissors at mid-thigh and grafted with a 60A protein (comprising, e.g., Seq. ID NO. 2) gel graft that separates the nerve stumps by 12 mm. The graft region is encased in a silicone tube 20 mm in length with a 1.5 mm inner diameter, the interior of which is filled with the morphogen solution. Specifically, The central 12 mm of the tube consists of an 60A protein (comprising, e.g., Seq. ID NO. 2) gel prepared by mixing 1 to 5 μg of substantially pure recombinantly produced 60A protein (comprising, e.g., Seq. ID NO. 2) with approximately 100 μl of MATRIGEL™ (from Collaborative Research, Inc., Bedford, Mass.), an extracellular matrix extract derived from mouse sarcoma tissue, and containing solubilized tissue basement membrane, including laminin, type IV collagen, heparin sulfate, proteoglycan and entactin, in phosphate-buffered saline. The morphogen-filled tube then is implanted directly into the defect site, allowing 4 mm on each end to insert the nerve stumps. Each stump is abutted against the morphogen gel and is secured in the silicone tube by three stitches of commercially available surgical 10-0 nylon through the epineurium, the fascicle protective sheath.

In addition to 60A protein (comprising, e.g., Seq. ID NO. 2) gel grafts, control grafts of empty silicone tubes, silicone tubes filled with gel only and "reverse" autografts, wherein 12 mm transected segments of the animal's sciatic nerve are rotated 180° prior to suturing, preferably also are grafted. All experiments preferably are performed in quadruplicate. All wounds preferably are closed by wound clips that are removed after 10 days. Rats can be grafted on both legs. At 3 weeks the animals are sacrificed, and the grafted segments removed and frozen on dry ice immediately. Frozen sections then are cut throughout the graft site, and examined for axonal regeneration by immunofluorescent staining using anti-neurofilament antibodies labeled with flurocein (obtained, for example, from Sigma Chemical Co., St. Louis).

Regeneration of the sciatic nerve is anticipated to occur across the entire 12 mm distance in all graft sites wherein the gap is filled with the 60A protein (comprising, e.g., Seq. ID NO. 2) gel. By contrast, empty silicone tubes, gel alone and reverse autografts do not show nerve regeneration.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A composition comprising:
   (a) a biocompatible, acellular matrix; and
   (b) a protein comprising:
      (i) the amino acid sequence of SEQ ID NO: 2; or
      (ii) a naturally occurring allelic variant of (i); or
      (iii) a fragment of (i) comprising a C-terminal six cysteine skeleton; or
      (iv) a conservative amino acid substitution variant of any of (i)–(iii),
   wherein said composition induces endochondral bone formation in an in vivo assay for bone formation.

2. The composition of claim 1 wherein said protein comprises amino acids 354 to 455 of SEQ ID NO: 2, or a conservative amino acid substitution variant thereof.

3. The composition of claim 1 wherein said protein comprises amino acids 326 to 455 of SEQ ID NO: 2, or a conservative amino acid substitution variant thereof.

4. The composition of claim 1 wherein said protein comprises amino acids 281 to 455 of SEQ ID NO: 2, or a conservative amino acid substitution variant thereof.

5. The composition of claim 1 wherein said protein comprises amino acids 20 to 455 of SEQ ID NO: 2, or a conservative amino acid substitution variant thereof.

6. The composition of claim 1 wherein said matrix is biodegradable.

7. The composition of claim 1 wherein said matrix is derived from tissue of the same type as that to which said composition is to be applied.

8. The composition of claim 1 wherein said matrix comprises collagen.

* * * * *